United States Patent
Li et al.

(10) Patent No.: US 6,174,995 B1
(45) Date of Patent: *Jan. 16, 2001

(54) HUMAN CHEMOKINES, CKβ4 AND CKβ10/MCP-4

(76) Inventors: Haodong Li, 18 Observation Ct., Fox Run 303, Germantown, MD (US) 20878; Mark Adams, 15205 Dufief Dr., North Potomac, MD (US) 20997; Solange Hanschke Lima, 13404 Fairland Park Dr., Silver Spring, MD (US) 20904; Ralph Alderson, 12125 Orchard View Rd., Gaithersburg, MD (US) 20878; Yuling Li, 12922 McCubbin La., Germantown, MD (US) 20874; David Parmelee, 11512 Parkedge Dr., Rockville, MD (US) 20852; John White, 332 Jennifer Dr., Coatsville, PA (US) 19320; Edward Applebaum, 830 Village Cir., Blue Bell, PA (US) 19422

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/613,822

(22) Filed: Feb. 23, 1996

Related U.S. Application Data

(63) Continuation-in-part of application No. 08/462,967, filed on Jun. 5, 1995, and a continuation-in-part of application No. 08/458,355, filed on Jun. 2, 1995, and a continuation-in-part of application No. PCT/US94/09484, filed on Aug. 23, 1994.

(51) Int. Cl.⁷ .......................... C07K 14/52; A61K 38/19
(52) U.S. Cl. .......................... 530/351; 530/324; 930/140; 424/85.1
(58) Field of Search ................................ 530/351, 324; 930/140; 424/85.1

(56) References Cited

U.S. PATENT DOCUMENTS

| | | |
|---|---|---|
| 4,897,348 | 1/1990 | Johnson et al. . |
| 5,278,287 | 1/1994 | Rollins . |
| 5,306,709 | 4/1994 | Gewirtz et al. . |
| 5,346,686 | 9/1994 | Lyle et al. . |
| 5,413,778 | 5/1995 | Kunkel et al. . |
| 5,474,983 | 12/1995 | Kuna et al. . |
| 5,602,008 | 2/1997 | Wilde et al. . |
| 5,936,068 * | 8/1999 | Wilde et al. ............... 530/351 |

FOREIGN PATENT DOCUMENTS

| | | |
|---|---|---|
| 0538 030 2 | 4/1993 | (EP) . |
| 07089866 | 4/1995 | (JP) . |
| WO90/06321 | 6/1990 | (WO) . |
| WO91/04274 | 4/1991 | (WO) . |
| WO91/12815 | 9/1991 | (WO) . |
| WO92/05198 | 4/1992 | (WO) . |
| WO92/20372 | 11/1992 | (WO) . |
| WO95/17092 | 6/1995 | (WO) . |
| WO95/31467 | 11/1995 | (WO) . |
| WO95/31468 | 11/1995 | (WO) . |
| WO96/05856 | 2/1996 | (WO) . |
| WO96/06169 | 2/1996 | (WO) . |
| WO96/09062 | 3/1996 | (WO) . |
| WO96/16979 | 6/1996 | (WO) . |
| WO98/01557 | 7/1996 | (WO) . |
| WO98/17800 | 10/1996 | (WO) . |
| WO98/21330 | 11/1996 | (WO) . |
| WO96/39520 | 12/1996 | (WO) . |
| WO96/39521 | 12/1996 | (WO) . |
| WO96/39522 | 12/1996 | (WO) . |
| WO97/31098 | 3/1997 | (WO) . |
| WO97/15594 | 5/1997 | (WO) . |
| WO97/15595 | 5/1997 | (WO) . |
| WO97/35982 | 10/1997 | (WO) . |
| WO/98/11226 | 3/1998 | (WO) . |
| WO98/09171 | 3/1998 | (WO) . |
| WO98/14573 | 4/1998 | (WO) . |

OTHER PUBLICATIONS

Berger, M.S. "Isolation of Monocyte Chemotactic Protein–4", *Clinical Research* 42(2):305A, Apr. 1994.*
Uguccioni, M., et al., "Monocyte Chemotactic Protein 4 (MCP–4), A Novel Structural and Functional Analogue of MCP–3 and Eotaxin", *J. Exp. Med.* 183(5):2379–2384, May 1, 1996.*
Widmer, U., et al., J. Immunology, 150:4996–5012 (1993).
Schall, T., et al., Eur. J. Imm. 22:1477–1481 (1992).
Furuta, R. et al., J. Biochem. 106: 436–441 (1989).
Brown, et al., J. Immunology, 142:679–687 (1989).
Kurdowska, A. et al., Cytokine, 6:124–134 (1994).
GenBank Accession No.: I35613 (Feb. 26, 1997).
GeneSeq Accession No.: W44398 (Jun. 11, 1998).
GeneSeq Accession No.: W61279 (Sep. 24, 1998).
GeneSeq Accession No.: W57475 (Sep. 7, 1998).
Jose et al *J. Exp Med* vol. 179, p. 881–87, Mar. 1994.*
Bischoff et al *J. Exp Med* 175, p. 1271–75, May 1992.*
Lukacs et al *J Exp Med* 177, p. 1551–59 Jun. 1993.*
Kurdowska et al *Cytokine* 6(2) 1994, p. 124–34.*

(List continued on next page.)

* cited by examiner

Primary Examiner—Garnette D. Draper
(74) Attorney, Agent, or Firm—Human Genome Sciences Inc.

(57) ABSTRACT

Human chemokine polypeptides and DNA/(RNA) encoding such chemokine polypeptides and a procedure for producing such polypeptides by recombinant techniques is disclosed. Also disclosed are methods for utilizing such chemokine polypeptides for the treatment of leukemia, tumors, chronic infections, autoimmune disease, fibrotic disorders, wound healing and psoriasis. Antagonists against such chemokine polypeptides and their use as a therapeutic to treat rheumatoid arthritis, autoimmune and chronic inflammatory and infective diseases, allergic reactions, prostaglandin-independent fever and bone marrow failure are also disclosed.

30 Claims, 10 Drawing Sheets

OTHER PUBLICATIONS

Geneseq Accession No: R93087 (27–Aug–96).
Geneseq Accession No: W22670 (19–Mar–98).
Geneseq Accession No: W30191 (21–May–98).
Geneseq Accession No: W56087 (17–Aug–98).
Geneseq Accession No: W56690 (23–Jul–98).
Geneseq Accession No: W57475 (07–Sep–98).
Geneseq Accession No: W44398 (11–Jun–98).
Geneseq Accession No: W61279 (24–Sep–98).
Geneseq Accession No: T90880 (21–May–98).
Geneseq Accession No: V28591 (17–Aug–98).
Geneseq Accession No: W17660 (16–Dec–97).
Geneseq Accession No: R95690 (20–Dec–96).
Geneseq Accession No: T90883 (21–May–98).
GenBank Accession No: U77035 (Jan–23–97).
GenBank Accession No: D86955 (Mar–06–97).
GenBank Accession No: U64197 (Jun–25–97).
GenBank Accession No: U46767 (Dec–14–96).
GenBank Accession No: X98306 (Jul–20–98).
Hieshima, K., et al., J. Immunol., vol. 159:1140–9 (1997).
Kodelja, V., et al., The J. Immunology, vol. 160:1411–1418 (1998).
Patel, V. P., et al., J. Exp Med., vol. 185:1163–1172 (1997).
Taub, D. D. et al., Therapeutic Immunology, vol. 1:229–246 (1994).
George et al., Macromolecular Sequencing & Synthesis, Ch. 12:127–149 (1988).
Craddock et al., Blood, vol. 90:4779–4788 (1997).
Liu et al., Blood, vol. 90:2522–2528 (1997).
Laterveer et al., Blood, vol. 87:781–788 (1996).
Laterveer et al., Exp. Hematology, vol. 24:1387–1393 (1996).
Blum, S. et al., DNA and Cell Biology, vol. 9:589–602 (1990).
Obaru, K., et al., J. Biochem., vol. 99:885–894(1986).
Derynck, R., et al., Biochemestry, vol. 29:10225–10233 (1990).
Sudo, K. et al., Genomics, vol. 24:276–276 (1994).
Kuna, P. et al., The J. of Exp. Med. vol. 175:489–493 (1992).
Matsushima, K. et al., The J. of Exp. Med. vol. 169:1485–1490 (1989).
Schall, T. J. et al., Cytokine, vol. 3:165–183 (1991).
Clements J. M., et al., Cytokine, vol. 4:72–82 (1992).
Zipfel, P.F., et al., The J. of immunology, Vol. 142:1582–1590 (1989).
Graham, G. J. et al., Development Biology, vol. 151:377–381 (1992).
Lerner, R. A. et al., Nature, vol. 299 (1982).
Nakao, M. et al., Molecular and Cellular Biology, vol. 10:3646–3658 (1990).
Kwon, Y. S. et al., Proc. Natl. Acad. Sci., vol. 86:1963–1967 (1989).
International Search Report, EP 97 30 3204 (Jan–23–98).
Wolpe, S. C. et al., Lab. of Med. Bioche. Rockefeller Univ. Press, vol. 175:3446–3658 (1990).
Glover, D. M. et al., Gene Cloning (1984).
Geneseq Accession No: AAC50943.1 (06–Aug–96).
Geneseq Accession No: AAB61534.1 (06–Aug–96).
Geneseq Accession No: AA739063 (14–Jan–98).
Geneseq Accession No: T27336 (06–Dec–94).
Geneseq Accession No: AI735669 (14–Jun–99).
Geneseq Accession No: T27433 (06–Dec–94).
Geneseq Accession No: D31065 (08–Feb–95).
Geneseq Accession No: AA297433 (18–Apr–97).
Geneseq Accession No: AJ001634 (10–Sep–97).
Geneseq Accession No: AJ000979 (30–Jun–97).
Geneseq Accession No: AC002482 (21–Aug–97).
Geneseq Accession No: Z77650 (30–Jul–96).
Geneseq Accession No: Z77651 (30–Jul–96).
Geneseq Accession No: CAA04888 (10–Sep–96).
Geneseq Accession No: CAB01111 (30–Jul–96).
Geneseq Accession No: CAB01112 (30–Jul–96).
Geneseq Accession No; AI925360 (02–Sep–99).
Geneseq Accession No: AA403048 (16–May–97).
Geneseq Accession No: AA404346 (16–May–97).
Geneseq Accession No: AA426245 (16–Oct–97).
Geneseq Accession No: T64262 (17–Feb–95).
Geneseq Accession No: T64134 (17–Feb–95).
Geneseq Accession No: D17181 (21–Jun–93).
Geneseq Accession No: R29479 (25–Apr–95).
European Search Report Application No. 99126093.6 date Apr. 14, 2000.
Opdenakker et al. (1993) Biochem. & Biophys. Res. Comms. 191(2):535–542.
Garcia–Zepeda et al., J. of Immumology, vol. 157(12)5613–5626 (1996).

```
ATGTGCTGTACCAAGAGTTTGCTCCTGGCTGCTCTTGATGTCAGTGCTGCTACTCCACCTC
 M  C  C  T  K  S  L  L  L  A  A  L  M  S  V  L  L  H  L

TGCGGCGAATCAGAAGCAGCAAGCAACTTTGACTGCTGTCTTGGATACACAGACCGTATT
 C  G  E  S  E  A  A  S  N  F  D  C  C  L  G  Y  T  D  R  I

CTTCATCCCTAAATTATTGTGGGCTTCACACGGCCAGCTGGCCAATGAAGGCTGTGACATC
 L  H  P  K  F  I  V  G  F  T  R  Q  L  A  N  E  G  C  D  I

AATGCTATCATCTTTCACACAAAGAAAAAGTTGTCTGTGTGCGCAAATCCAAAACAGACT
 N  A  I  I  F  H  T  K  K  K  L  S  V  C  A  N  P  K  Q  T

TGGGTGAAATATATTGTGCGTCTCCTCAGTAAAAAAGTCAAGAACATGTAA
 W  V  K  Y  I  V  R  L  L  S  K  K  V  K  N  M  *
```

FIG. 1

ATGAAAGTTTCTGCAGTGCTTCTGTGCTGCTCATGACAGCAGCTTCAACCCCCAG
 M  K  V  S  A  V  L  L  C  L  L  L  M  T  A  A  F  N  P  Q (pyroQ)

GGACTTGCTCAGCCAGATGCACTCAACGTCCCATCTACTTGCTTCACATTAGCAGT
 G  L  A  Q  P  D  A  L  N  V  P  S  T  C  C  F  T  F  S  S
      (pyroQ)

AAGAAGATCTCCCTTGCAGAGGCTGAAGAGCTATGTGATCACCAGCAGGTGTCCCAG
 K  K  I  S  L  Q  R  L  K  S  Y  V  I  T  S  R  C  P  Q

AAGGCTGTCATCTTCAGAACCAAACTGGGCAAGGAGATCTGTGCTGACCCCAAGGAGAAG
 K  A  V  I  F  R  T  K  L  G  K  E  I  C  A  D  P  K  E  K

TGGGTCCAGAATTATATGAAACACCTGGGCCGAAAGCTCACACCCTGAAGACTTGA
 W  V  Q  N  Y  M  K  H  L  G  R  K  A  H  T  L  K  T  *

FIG.2

```
25  EAASNFDCCLGYTDRILHPKFIVGFTRQLANEGCDINAIIFHTKKKLSVC  74
     :|  :| : :|  :  :  ::  ::  ||::::| : |:: :|: 
 1  HPGIPSACCFRVTNICKISFQALKSYKIITSSKCPQTAIVFEIKPDKMIC  50

75  ANPKQTWVKYIVRLLSKKVK  94
    |:|   ||  :|  :|:: 
51  ADPRXXWVQDAKKYLDQISQ  70
```

FIG. 3

```
 1  MKVSAVLLCLLLMTAAFNPQGLAQPDALNVPSTCCFTFSSKKISLQRLKS  50
    |:| | ||||| ||||:|||||||  |||||||:|  ||||| || ||| 
 1  MKASAALLCLLLTAAAFSPQGLAQPVGINTSTCCYRFINKKIPKQRLES  50

51  YVITT.SRCPQKAVIFRTKLGKEICADPKEKWVQNYMKHLGRKAHTLKT  98
    | ||| | ||:|||| ||:||||||||  ||| | ||||:|: | ||| 
51  YRRTTSSHCPREAVIFKTKLDKEICADPTQKWVQDFMKHLDKKTQTPKL  99
```

FIG. 4

MCP-4 POLYPEPTIDES

| | | | | | | |
|---|---|---|---|---|---|---|
| cDNA | MKVSAVLLCL LLMTAAFNPQ | GLAQPDALNV | PSTCCFTFSS | KKISLQRLKS | YVITTSRCPQ | KAVIFRTKLG | KEICADPKEK | WVQNYMKHLG | RKAHTLKT |
| Bac 1 | ......FNPQ | GLAQPDALNV | PSTCCFTFSS | KKISLQRLKS | YVITTSRCPQ | KAVIFRTKLG | KEICADPKEK | WVQNYMKHLG | RKAHTLKT |
| Bac 2 | .LAQPDALNV | PSTCCFTFSS | KKISLQRLKS | YVITTSRCPQ | KAVIFRTKLG | KEICADPKEK | WVQNYMKHLG | RKAHTLKT |
| Bac 3 | ...*QPDALNV | PSTCCFTFSS | KKISLQRLKS | YVITTSRCPQ | KAVIFRTKLG | KEICADPKEK | WVQNYMKHLG | RKAHTLKT |
| Dro1 | ...*Q GLAQPDALNV | PSTCCFTFSS | KKISLQRLKS | YVITTSRCPQ | KAVIFRTKLG | KEICADPKEK | WVQNYMKHLG | RKAHTLKT |
| Dro2 | GLAQPDALNV | PSTCCFTFSS | KKISLQRLKS | YVITTSRCPQ | KAVIFRTKLG | KEICADPKEK | WVQNYMKHLG | RKAHTLKT |
| Dro3+ | ......LNV | PSTCCFTFSS | KKISLQRLKS | YVITTSRCPQ | KAVIFRTKLG | KEICADPKEK | *WVQNYMKHLG* | *RKAHTLKT* |

* GLUTAMINE OR PYROGLUTAMATE
ITALICS HETEROGENEOUS CARBOXYL TERMINI

HOMOLOGY COMPARISONS

| | | | | | | | | |
|---|---|---|---|---|---|---|---|---|
| MCP-3 | ....QPVGINT | STTCCYRFIN | KKIPKQRLES | YRRTTSSHCPR | EAVIFKTKLD | KEICADPTQK | WVQDFMKHLD | KKTQTPKL |
| MCP-4 | MKVSAVLLCL LLMTAAFNPQ | GLAQPDALNV | PSTCCFTFSS | KKISLQRLKS | YVITT-SRCPQ | KAVIFRTKLG | KEICADPKEK | *WVQNYMKHLG* | *RKAHTLKT* |
| Eotaxin | ......GPASV | PTTCCFNLAN | RKIPLQRLES | YRRITSGKCPQ | KAVIFKTKLA | KDICADPKKK | WVQDSMKYLD | QKSPTPKP |

FIG. 5

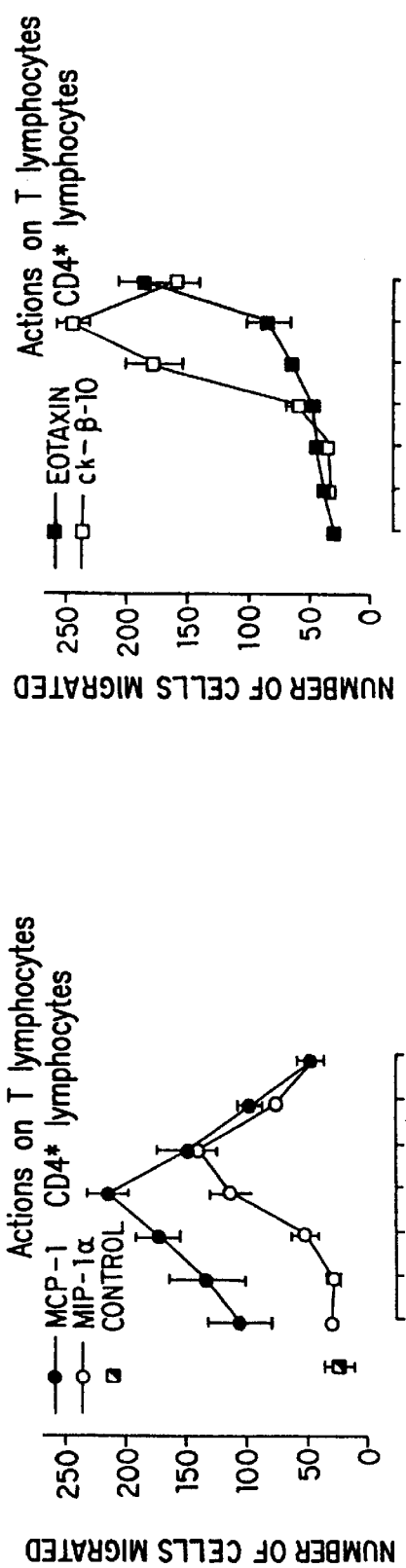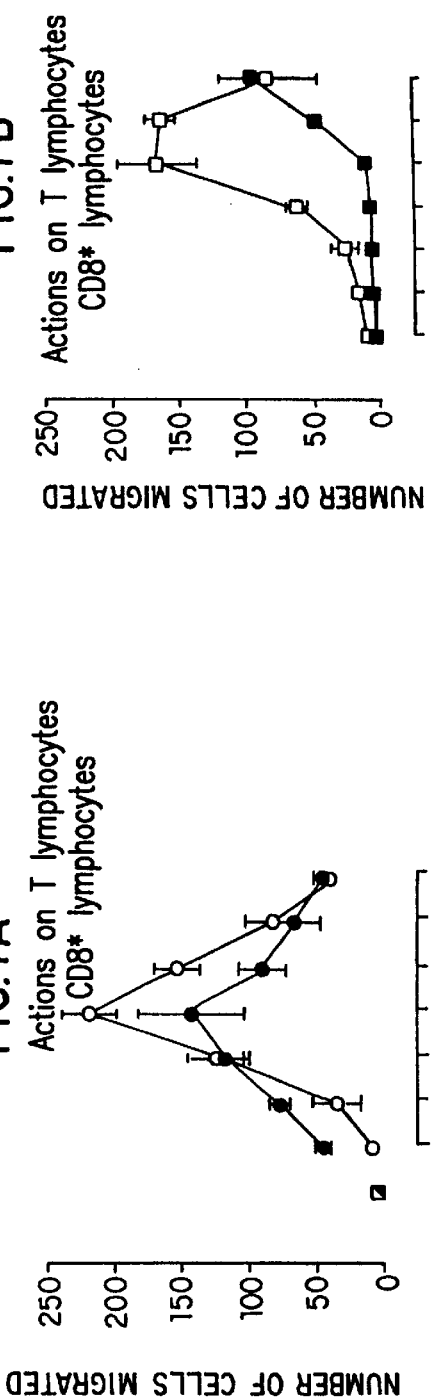

Ckβ-4 [ng/ml]

HUMAN CHEMOKINES, CKβ4 AND CKβ10/ MCP-4

This application is a continuation-in-part of U.S. patent application Ser. No. 08/462,967 filed on Jun. 5, 1995 and of U.S. patent application Ser. No. 08/458,355 filed on Jun. 2, 1995 and of PCT application PCT/US94/09484, of which priority is claimed in the aforementioned two U.S. patent applications, all of which are incorporated by reference herein in their entirety.

This invention relates to newly identified polynucleotides, polypeptides encoded by such polynucleotides, the use of such polynucleotides and polypeptides, as well as the production of such polynucleotides and polypeptides. More particularly, the polypeptides of the present invention are human chemokine beta-4 (also referred to as "Ckβ-4") and human chemokine monocyte chemotactic protein (referred to as "MCP-4," and also known and referred to as human chemokine beta-10 and "Ckβ-10"), which, collectively, are referred to as "the chemokine polypeptides". The invention also relates to inhibiting the action of such polypeptides.

Chemokines are an emerging super-family of small secreted cytokines that are structurally and functionally related. All chemokines exhibit 25 to 75% homology at the amino acid level and contain spatially conserved cysteine residues as do the polypeptides of the present invention. Members of the "C-X-C branch" (according to the position of the first two cysteines in the conserved motif), also known as neutrophil-activating peptide (NAP)/IL-8 family, exert pro-inflammatory activity mainly through their action on neutrophils (e.g., IL-8 and NAP-2), whereas members of the "C-C branch" family appear to attract certain mononuclear cells. Members of the "C-C branch" include PF4, MIPs, MCPs, and the chemokine polypeptides of the present invention.

Numerous biological activities have been assigned to this chemokine family. The macrophage inflammatory protein 1α and 1β are chemotactic for distinct lymphocyte populations and monocytes (Schall, T. J., Cytokine, 3:165 (1991)), while MCP-1 has been described as a specific monocyte chemo-attractant (Matsushima et al., J. Exp. Med., 169: 1485 (1989)). The common function of this chemokine family is their ability to stimulate chemotactic migration of distinct sets of cells, for example, immune cells (leukocytes) and fibroblasts. These chemokines are also able to activate certain cells in this family.

The immune cells which are responsive to the chemokines have a vast number of in vivo functions and therefore their regulation by such chemokines is an important area in the treatment of disease.

For example, eosinophils destroy parasites to lessen parasitic infection. Eosinophils are also responsible for chronic inflammation in the airways of the respiratory system. Macrophages are responsible for suppressing tumor formation in vertebrates. Further, basophils release histamine which may play an important role in allergic inflammation. Accordingly, promoting and inhibiting such cells, has wide therapeutic application.

In accordance with one aspect of the present invention, there are provided novel polypeptides which are Ckβ-4, and MCP-4 (also referred to as Ckβ-10), as well as fragments, analogs and derivatives thereof. The polypeptides of the present invention are of human origin.

In accordance with another aspect of the present invention, there are provided polynucleotides (DNA or RNA) which encode such polypeptides.

In accordance with yet a further aspect of the present invention, there is provided a process for producing such polypeptides by recombinant techniques.

In accordance with yet a further aspect of the present invention, there is provided a process for utilizing such polypeptides, or polynucleotides encoding such polypeptides for therapeutic purposes, for example, to treat solid tumors, chronic infections, auto-immune diseases, psoriasis, asthma, allergy, to regulate hematopoiesis, and to promote wound healing.

In accordance with yet a further aspect of the present invention, there are provided antibodies against such polypeptides.

In accordance with yet another aspect of the present invention, there are provided antagonist/inhibitors to such polypeptides, which may be used to inhibit the action of such polypeptides, for example, in the treatment of auto-immune diseases, chronic inflammatory and infective diseases, histamine-mediated allergic reactions, prostaglandin-independent fever, bone marrow failure, silicosis, sarcoidosis, hyper-eosinophilic syndrome and lung inflammation.

These and other aspects of the present invention should be apparent to those skilled in the art from the teachings herein.

The following drawings are illustrative of embodiments of the invention and are not meant to limit the scope of the invention as encompassed by the claims.

BRIEF DESCRIPTION OF THE FIGURES

FIG. 1 displays the cDNA sequence and corresponding deduced amino acid sequence of Ckβ-4. The initial 24 amino acids represent the deduced leader sequence of Ckβ-4 such that the putative mature polypeptide comprises 70 amino acids. The standard one-letter abbreviation for amino acids is used.

FIG. 2 displays the cDNA sequence and corresponding deduced amino acid sequence of MCP-4 (also referred to as Ckβ-10). The initial 23 amino acids represent the putative leader sequence of MCP-4 (Ckβ-10) such that the putative mature polypeptide comprises 75 amino acids. As noted in FIG. 5, however, there are several amino terminal ends of MCP-4 produced in cells, represented by arrows in FIG. 1, as shown in FIG. 5 and as discussed herein. In addition several carboxyl terminus have been observed in certain forms of MCP-4 and produced in cells; shown in FIG. 5 and discussed herein. The standard one-letter abbreviation for amino acids is used.

FIG. 3 displays the amino acid sequence homology between Ckβ-4 and the mature peptide of eotaxin (bottom). The standard one-letter abbreviation for amino acids is used.

FIG. 4 displays the amino acid sequence homology between human MCP-4 (Ckβ-10) (top) and human MCP-3 (bottom). The standard one-letter abbreviation for amino acids is used.

FIG. 5 shows the amino acid sequences of several different forms of MCP-4 (Ckβ-10) isolated by expression in vitro. Bac1, 2 and 3 show sequences of three $NH_2$-terminal variants of MCP-4 expressed using baculovirus. Dro1, 2 and 3+ show sequences of MCP-4 isolated by expression of MCP-4 cDNA in Drosophila cells in vitro. The figure also shows an homology comparison of the full length MCP-4 sequence with sequences of MCP-3 and eotaxin. Identical residues are indicated by vertical lines.

Enzyme activity is presented on a linear scale of arbitrary fluorescence units along the vertical axis in (A). Relative migration index is presented on a linear scale on the vertical axis in (B) Chemokine concentration in nM is presented in both graphs on a log scale along the horizontal axis.

As discussed in the examples below, cell migration was measured in 48 well chemotaxis chambers. The migrating cells were counted in five high power fields. The migration is expressed as migration index (mean of migrated cells/ mean of migrated cells in absence of added chemokine). Each point is the average of three replicate cultures. The bar shows the standard deviation about the average for the three cultures.

FIG. 7 is a set of graphs showing migration of CD4+ and CD8+ T-lymphocytes in response to various concentrations of MCP-4 (Ckβ-10), Eotaxin, MCP-1, MIP-1α and a negative control. Upper graphs show migration of CD4+ T-lymphocytes. Lower graphs show migration of CD8+ T-lymphocytes. In both upper and lower pairs the left graph shows migration in response to MCP-1, MIP-1α and a negative control and the right graph shows migration in response to MCP-4 (Ckβ-10), Eotaxin. Number of migrating cells is indicted on a linear scale along the vertical axis. Chemokine concentrations in the attractant media are indicated in nM on a log scale along the horizontal axis.

As discussed in the examples below, cell migration was measured in 48 well chemotaxis chambers. The migrating cells were counted in five high power fields. The migration is expressed as migration index (mean of migrated cells/ mean of migrated cells in absence of added chemokine). Each point is the average of three replicate cultures. The bar shows the standard deviation about the average for the three cultures.

Figure 8B:
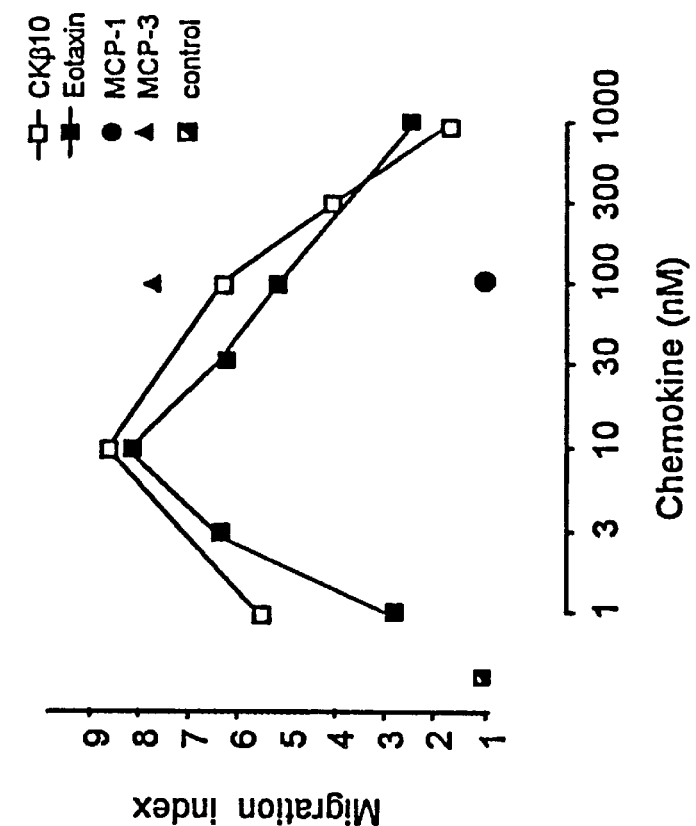
Figure 8A:
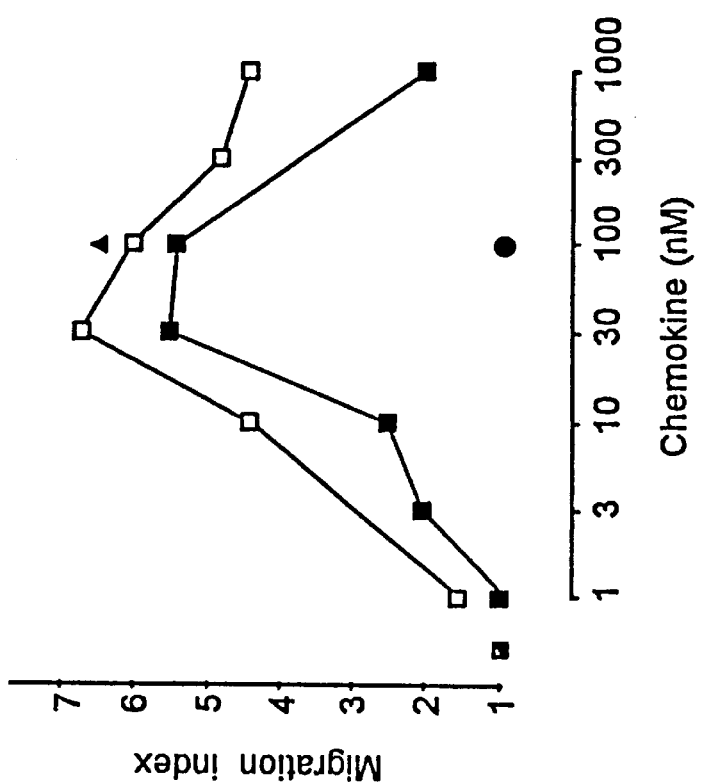

FIG. 8 provides a pair of graphs showing the migration of human eosinophils in response to a negative control, 100 nM MCP-1, 100 nM MCP-3 and several concentration of MCP-4 (Ckβ-10) and Eotaxin. Migration index is indicted on a linear scale along the vertical axis. Chemokine concentrations in the attractant media are indicated in nM on a log scale along the horizontal axis.

As discussed in the examples below, cell migration was measured in 48 well chemotaxis chambers. The migrating cells were counted in five high power fields. The migration is expressed as migration index (mean of migrated cells/ mean of migrated cells in absence of added chemokine). Each point is the average of three replicate cultures. The bar shows the standard deviation about the average for the three cultures.

Figure 9:
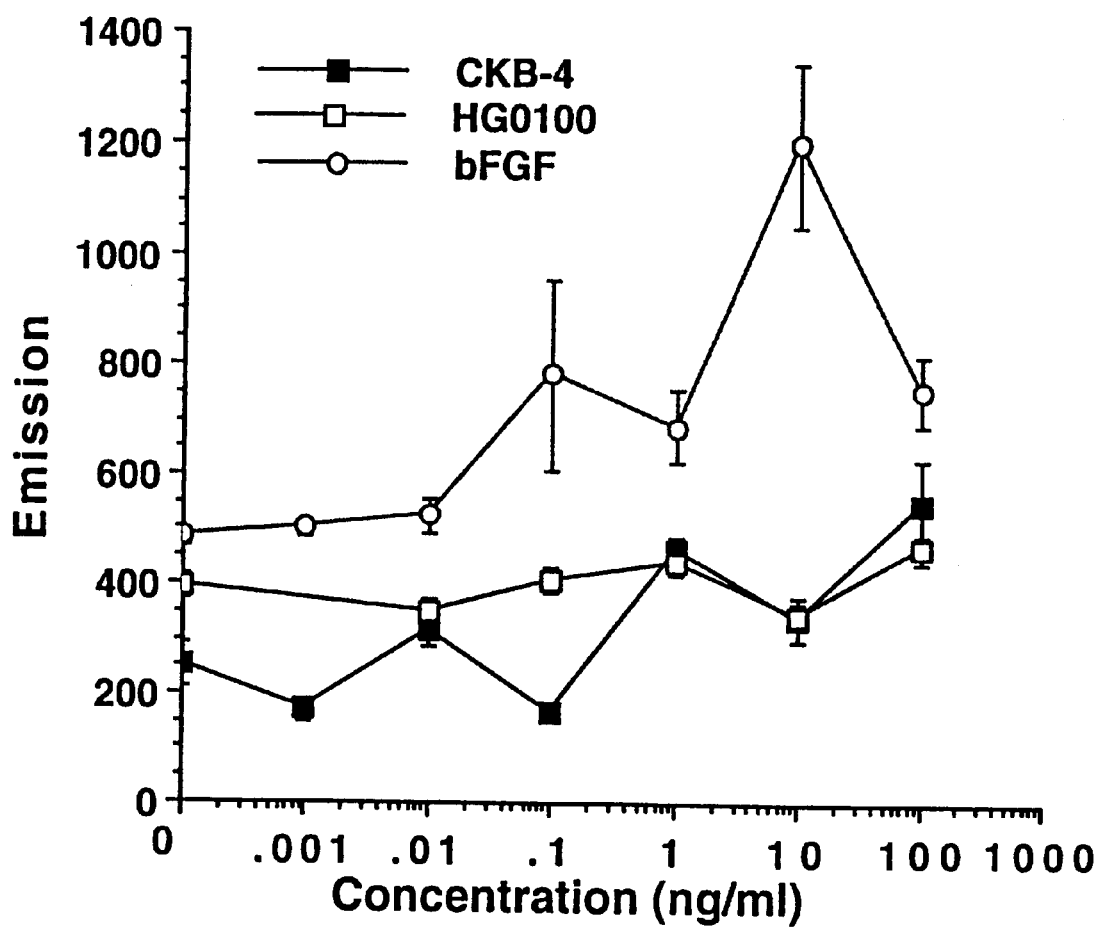

FIG. 9 is a graph showing survival of cortical neuronal cells cultured in the presence of various concentrations of Ckβ-4, Basic FGF and HG0100. The number of viable cell counts are indicted on a linear scale along the vertical axis, in terms of calcein emission. Concentrations of the factors in the growth medium are indicated in ng/ml on a log scale along the horizontal axis. Each point is the average of six replicate cultures. The bar shows the standard error of the mean about the average for the six cultures.

Figure 10:
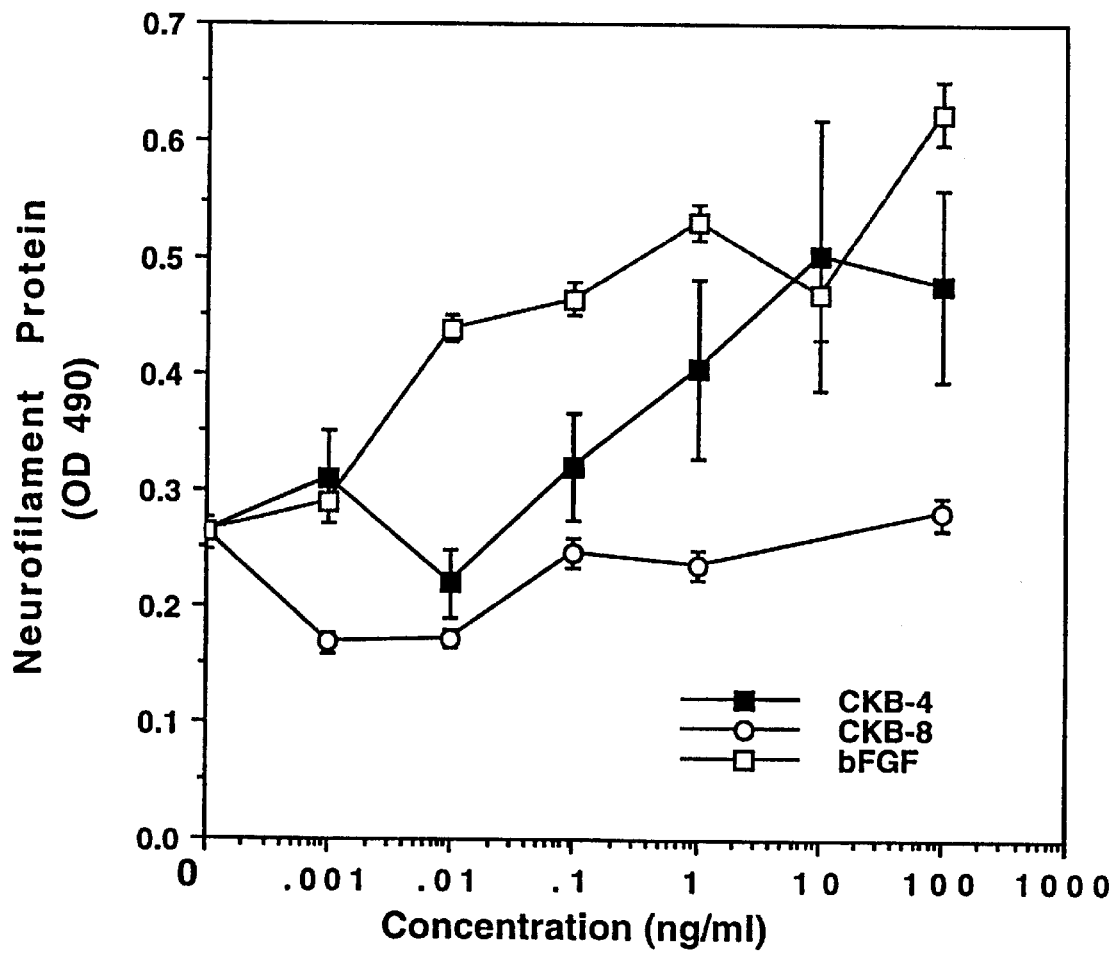

FIG. 10 is a graph showing neurite outgrowth of cortical neurons cultured in the presence of various concentrations of Ckβ-4, Basic FGF and HG0100. Neurite outgrowth is indicted on a linear scale along the vertical axis, in terms of neurofilament protein measured optical density at 490 nm ($OD^{490}$) Concentrations of the factors in the growth medium are indicated in ng/ml on a log scale along the horizontal axis. Each point is the average of six replicate cultures. The bar shows the standard error of the mean about the average for the six cultures.

Figure 11A:
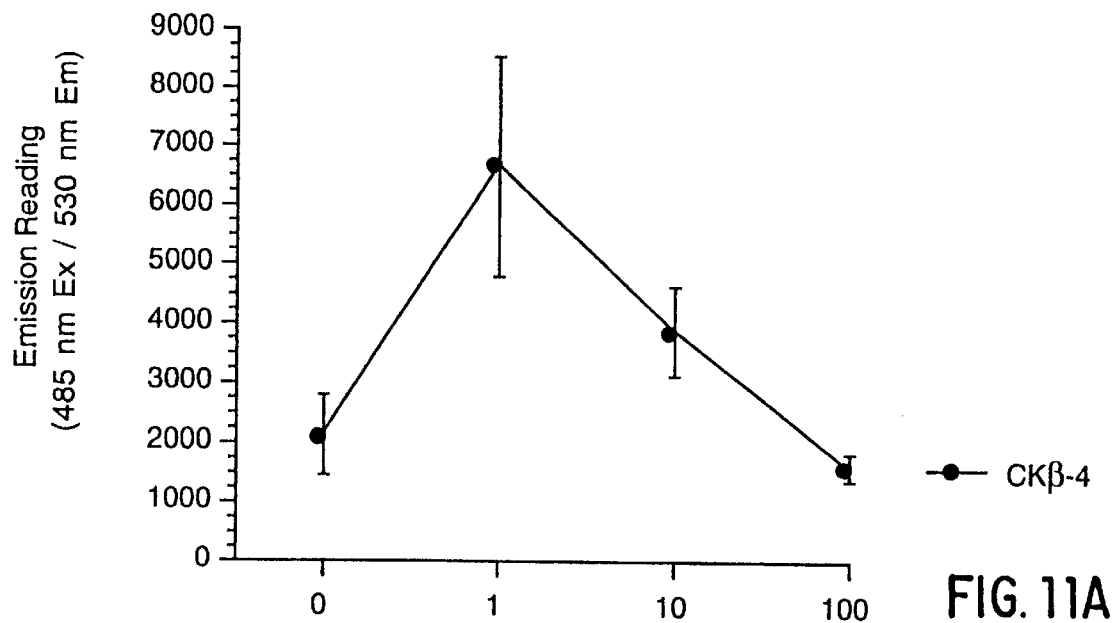
Figure 11B:
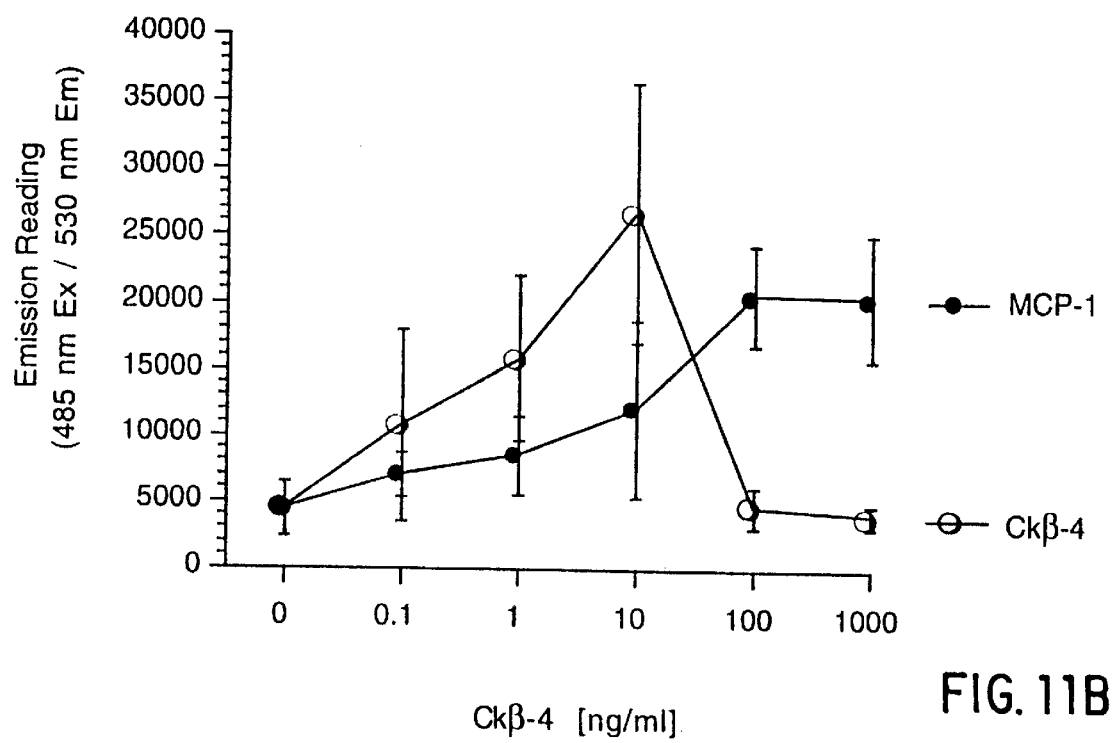

FIG. 11 is a graph showing chemotaxis of peripheral blood lymphocytes in response to cultured in the presence of various concentrations of Ckβ-4 and MCP-1. In each graph chemotaxis is indicted on a linear scale along the vertical axis, in terms of ratio of fluorescence emission at 530 nm stimulated by 485 nm excitation. Concentrations of the factors in the growth medium are indicated in ng/ml on a log scale along the horizontal axis. Each point is the average of several; replicate cultures. The bar shows the standard error of the mean about the average for the cultures.

In accordance with an aspect of the present invention, there are provided isolated nucleic acids (polynucleotides) which encode for the mature Ckβ-4 polypeptide having the deduced amino acid sequence of FIG. 1 or for the mature polypeptide encoded by the cDNA of the clone deposited as ATCC Deposit No. 75848 on Jul. 29, 1994 and for the mature MCP-4 (also known as Ckβ-10) polypeptide having the deduced amino acid sequence of FIGS. 2 and 5 or for the mature polypeptide encoded by the cDNA of the clone deposited as ATCC Deposit No. 75849 on Jul. 29, 1994. Also provided in accordance with this aspect of the invention are polynucleotides encoding MCP-4 polypeptides comprising in sequence residues 28–93 set out in FIGS. 2 and 5 and, among these, particularly polynucleotides encoding a polypeptide having an amino acid sequence selected from the group consisting of residues 1–98, 17–98, 20–98, 22–98, 24–98, 28–98, 28–95 and 28–93 set out in FIGS. 2 and 5 and fragments, analogs and derivatives thereof.

The polynucleotide encoding Ckβ-4 was discovered in a cDNA library derived from a human gall bladder. Ckβ-4 is structurally related to the chemokine family. It contains an open reading frame encoding a protein of 96 amino acid residues of which the first 26 amino acids residues are the putative leader sequence such that the mature protein comprises 70 amino acids. The protein exhibits the highest degree of homology to eotaxin with 20% identity and 37% similarity over the entire coding sequence. It is also important that the four spatially conserved cysteine residues in chemokines are found in the polypeptides of the present invention.

The polynucleotide encoding MCP-4 (also known as Ckβ-10) was discovered in a cDNA library derived from nine week early human tissue. MCP-4 is structurally related to the chemokine family. It contains an open reading frame encoding a protein of 98 amino acid residues of which approximately the first 20 amino acid residues are putative or actual leader sequences as shown in FIG. 5 and discussed elsewhere herein, and the mature protein comprises around 75 amino acids depending on the cleavage site, or sites, also as shown in FIG. 5. The protein has a marked sequence similarity to MCP-1, MCP-2, MCP-3 and Eotaxin and exhibits the highest degree of homology to MCP-3 with 65% identity and 77% similarity over the entire coding sequence.

Particularly preferred MCP-4 polypeptides (also referred to herein as Ckβ-10) of the present invention, described herein below in greater detail, include polypeptides having the amino acid sequences set out in FIG. 2 or FIG. 5. It will be appreciated that such preferred polypeptides include those with free amino and blocker amino termini, particular those noted in FIG. 5, in which the terminal glutamine is a blocked pyroglutamine residue. In accordance with this aspect of the invention are preferred MCP-4 polypeptides comprising in sequence residues 28–93 set out in FIGS. 2 or 5 and, among these, particularly polypeptides having an amino acid sequence selected from the group consisting of residues 1–98, 17–98, 20–98, 22–98, 24–98, 28–98, 28–95 and 28–93 set out in FIGS. 2 or 5 and fragments, analogs and derivatives thereof.

Such polypeptides may be produced by expressing a cDNA of the invention, particularly a cDNA having the sequence set out in FIGS. 1, 2 or 5 or having the sequence of the human cDNA of the deposited clones, using for instance a baculovirus vector in insect host cells.

The polynucleotides of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. The coding sequence which encodes the mature polypeptides may be identical to the coding sequence shown in FIGS. 1 and 2 or that of the deposited clones or may be a different coding sequence which coding sequence, as a result of the redundancy or degeneracy of the genetic code, encodes the same mature polypeptides, or the other polypeptides noted herein, as for instance noted herein above, as the DNA of FIGS. 1, 2 or 5 or the deposited cDNAs.

The polynucleotide which encodes polypeptides of FIGS. 1, 2 or 5, and as noted elsewhere herein, or for the polypeptides encoded by the deposited cDNAs, may include: only the coding sequence for the mature polypeptide; the coding sequence for the mature polypeptide and additional coding sequence such as a leader or secretory sequence or a proprotein sequence; the coding sequence for the mature polypeptide (and optionally additional coding sequence) and non-coding sequence, such as introns or non-coding sequence 5' and/or 3' of the coding sequence for the mature polypeptides.

Thus, the term "polynucleotide encoding a polypeptide" encompasses a polynucleotide which includes only coding sequence for the polypeptide as well as a polynucleotide which includes additional coding and/or non-coding sequence.

The present invention further relates to variants of the hereinabove described polynucleotides which encode for fragments, analogs and derivatives of the polypeptide having the deduced amino acid sequence of FIGS. 1 and 2, and the sequences set out in FIG. 5, or the polypeptides encoded by the cDNA of the deposited clones. The variant of the polynucleotides may be a naturally occurring allelic variant of the polynucleotides or a non-naturally occurring variant of the polynucleotides.

Thus, the present invention includes polynucleotides encoding the same mature polypeptides as shown in FIGS. 1 and 2, the polypeptides set out in FIG. 5, or the same mature polypeptides encoded by the cDNA of the deposited clones as well as variants of such polynucleotides which variants encode for a fragment, derivative or analog of the polypeptides of FIGS. 1 and 2, or the polypeptides set out in FIG. 5, or the polypeptides encoded by the cDNA of the deposited clones. Such nucleotide variants include deletion variants, substitution variants and addition or insertion variants.

As hereinabove indicated, the polynucleotides may have a coding sequence which is a naturally occurring allelic variant of the coding sequence shown in FIGS. 1 and 2, or the polypeptides set out in FIG. 5, or of the coding sequence of the deposited clones. As known in the art, an allelic variant is an alternate form of a polynucleotide sequence which may have a substitution, deletion or addition of one or more nucleotides, which does not substantially alter the function of the encoded polypeptide.

The present invention also includes polynucleotides, wherein the coding sequence for the mature polypeptides may be fused in the same reading frame to a polynucleotide sequence which aids in expression and secretion of a polypeptide from a host cell, for example, a leader sequence which functions as a secretory sequence for controlling transport of a polypeptide from the cell. The polypeptide having a leader sequence is a preprotein and may have the leader sequence cleaved by the host cell to form the mature form of the polypeptide. The polynucleotides may also encode for a proprotein which is the mature protein plus additional 5' amino acid residues. A mature protein having a prosequence is a proprotein and is an inactive form of the protein. Once the prosequence is cleaved an active mature protein remains.

Thus, for example, the polynucleotide of the present invention may encode for a mature protein, or for a protein having a prosequence or for a protein having both a prosequence and a presequence (leader sequence).

The polynucleotides of the present invention may also have the coding sequence fused in frame to a marker sequence which allows for purification of the polypeptides of the present invention. The marker sequence may be a hexa-histidine tag supplied by a pQE-9 vector to provide for purification of the mature polypeptides fused to the marker in the case of a bacterial host, or, for example, the marker sequence may be a hemaglutinin (HA) tag when a mammalian host, e.g. COS-7 cells, is used. The HA tag corresponds to an epitope derived from the influenza hemagglutinin protein (Wilson, I., et al., Cell, 37:767 (1984)).

The present invention further relates to polynucleotides which hybridize to the hereinabove-described sequences if there is at least 50% and preferably 70% identity between the sequences. The present invention particularly relates to polynucleotides which hybridize under stringent conditions to the hereinabove-described polynucleotides. As herein used, the term "stringent conditions" means hybridization will occur only if there is at least 95% and preferably at least 97% identity between the sequences. The polynucleotides which hybridize to the hereinabove described polynucleotides in a preferred embodiment encode polypeptides which retain substantially the same biological function or activity as the mature polypeptide encoded by the cDNA of FIGS. 1 and 2, or the polypeptides set out in FIG. 5, or the deposited cDNA.

The deposit(s) referred to herein will be maintained under the terms of the Budapest Treaty on the International Recognition of the Deposit of Micro-organisms for purposes of Patent Procedure. These deposits are provided merely as convenience to those of skill in the art and are not an admission that a deposit is required under 35 U.S.C. §112. The sequence of the polynucleotides contained in the deposited materials, as well as the amino acid sequence of the polypeptides encoded thereby, are incorporated herein by reference and are controlling in the event of any conflict with any description of sequences herein. A license may be required to make, use or sell the deposited materials, and no such license is hereby granted.

The present invention further relates to chemokine polypeptides which have the deduced amino acid sequences of FIGS. 1 and 2 or which has the amino acid sequence encoded by the deposited cDNA, as well as fragments, analogs and derivatives of such polypeptides.

The terms "fragment," "derivative" and "analog" when referring to the polypeptides of FIGS. 1 and 2 or that encoded by the deposited cDNA, means polypeptides which retain essentially the same biological function or activity as such polypeptides. Thus, an analog includes a proprotein which can be activated by cleavage of the proprotein portion to produce an active mature polypeptide.

The chemokine polypeptides of the present invention may be recombinant polypeptides, natural polypeptides or a synthetic polypeptides, preferably recombinant polypeptides.

The fragment, derivative or analog of the polypeptides of FIGS. 1 and 2, or of the polypeptides of FIG. 5, or that encoded by the deposited cDNAs may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as a leader or secretory sequence or a sequence which is employed for purification of the mature polypeptide or a proprotein sequence. Such fragments, derivatives and analogs are deemed to be within the scope of those skilled in the art from the teachings herein.

The polypeptides and polynucleotides of the present invention are preferably provided in an isolated form, and preferably are purified to homogeneity.

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The present invention also relates to vectors which include polynucleotides of the present invention, host cells which are genetically engineered with vectors of the invention and the production of polypeptides of the invention by recombinant techniques.

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the Ckβ-4 and MCP-4 genes (also referred to as Ckβ-10 genes). The culture conditions, such as temperature, pH and the like, are those previously used with the host cell selected for expression, and will be apparent to the ordinarily skilled artisan.

The polynucleotides of the present invention may be employed for producing polypeptides by recombinant techniques. Thus, for example, the polynucleotide may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the $E.$ $coli.$ lac or trp, the phage lambda PL promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in $E.$ $coli.$ The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as $E.$ $coli$, Streptomvces, *Salmonella tvohimurium*; fungal cells, such as yeast; insect cells such as Drosophila and Sf9; animal cells such as CHO, COS or Bowes melanoma; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example. Bacterial: pQE70, pQE60, pQE-9 (Qiagen), pBS, pD10, phagescript, psiX174, pbluescript SK, pbsks, pNH8A, pNH16a, pNH18A, pNH46A (Stratagene); ptrc99a, pKK223-3, pKK233-3, pDR540, pRIT5 (Pharmacia). Eukaryotic: pWLNEO, pSV2CAT, pOG44, pXT1, pSG (Stratagene) pSVK3, pBPV, pMSG, pSVL (Pharmacia). However, any other plasmid or vector may be used as long as they are replicable and viable in the host.

Promoter regions can be selected from any desired gene using CAT (chloramphenicol acctyl transferase) vectors or other vectors with selectable markers. Two appropriate vectors are pKK232-8 and pCM7. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation. (Davis, L., Dibner, M., Battey, I., Basic Methods in Molecular Biology, (1986)).

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989), the disclosure of which is hereby incorporated by reference.

Transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Examples including the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of E. coli and S. cerevisiae TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include E. coli, Bacillus subtilis, Salmonella typhimurium and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and pGEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well know to those skilled in the art.

Various mammalian cell culture systems can also be employed to express recombinant protein. Examples of mammalian expression systems include the COS-7 lines of monkey kidney fibroblasts, described by Gluzman, Cell, 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The chemokine polypeptides can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography hydroxylapatite chromatography and lectin chromatography. Protein refolding steps can be used, as necessary, in completing configuration of the mature protein. Finally, high performance liquid chromatography (HPLC) can be employed for final purification steps.

The chemokine polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated or may be non-glycosylated. Polypeptides of the invention may also include an initial methionine amino acid residue.

The chemokine polypeptides may be used to inhibit bone marrow stem cell colony formation as adjunct protective treatment during cancer chemotherapy and for leukemia.

They may also be used to regulate hematopoiesis, by regulating the activation and differentiation of various hematopoietic progenitor cells.

The chemokine polypeptides may also be used to inhibit epidermal keratinocyte proliferation for treatment of psoriasis, which is characterized by keratinocyte hyperproliferation.

The chemokine polypeptides may also be used to treat solid tumors by stimulating the invasion and activation of host defense cells, e.g., CD8$^+$, cytotoxic T cells and macrophages. Particularly, Ckβ-4 on peripheral blood lymphocytes and MCP-4 (also referred to as Ckβ-10) on CD8$^+$ T-cells, eosinophils and monocycles. They may also be used to enhance host defenses against resistant chronic infections, for example, mycobacteria, listeria or leishmania infections, or opportunistic infections such as, for example, cryptococcus infections, via the attraction of microbicidal leukocytes, such as peripheral blood leukocytes ("PBLs") by CKP-4 and CD4+T-cells, monocytes and eosinophils by MCP-4.

The chemokine polypeptides also increase the presence of eosinophils which have the distinctive function of killing the larvae of parasites that invade tissues, as in schistosomiasis, trichinosis and ascariasis.

The chemokine polypeptides may also be used to treat auto-immune disease and lymphocytic leukemias by inhibiting T cell proliferation by the inhibition of IL-2 biosynthesis.

Ckβ-4 and MCP-4 (also referred to as Ckβ-10) may also be used in wound healing, both via the recruitment of debris clearing and connective tissue promoting inflammatory cells and also via its control of excessive TGFP-mediated fibrosis. In this same manner, Ckβ-4 and MCP-4 may also be used to treat other fibrotic disorders, including liver cirrhosis, osteoarthritis and pulmonary fibrosis.

Chemokines may also be employed as inhibitors of angiogenesis, therefore, they have anti-tumor effects.

Chemokines of the present invention also may be used to enhance neuronal survival and differentiation and they may be employed, where effective in this regard, in the treatment of neurodegenerative diseases. Thus, for instance, Ckβ-4 may be used, where effective, to enhance neuton survival and neurite outgrowth.

The chemokine polypeptides of the present invention are also useful for identifying other molecules which have similar biological activity. An example of a screen for this is isolating the coding region of the genes by using the known DNA sequence to synthesize oligonucleotide probes. Labeled oligonucleotides having a sequence complementary to that of the genes of the present invention are used to screen a library of human cDNA, genomic DNA or mRNA to determine which members of the library the probe hybridizes to.

The present invention also relates to a diagnostic assays for detecting altered levels of the polypeptides or the MRNA which provides the message for such polypeptides, both quantitatively and qualitatively. Such assays are well-known in the art and include an ELISA assay, the radioimmunoassay and RT-PCR. The levels of the polypeptides, or their mRNAs, which are detected in the assays may be employed for the elucidation of the significance of the polypeptides in various diseases and for the diagnosis of diseases in which altered levels of the polypeptides may be significant.

This invention provides a method for identification of the receptors for the polypeptides. The gene encoding the receptors can be identified by expression cloning. Polyadenylated RNA is prepared from a cell responsive to the polypeptides, and a cDNA library created from this RNA is divided into pools and used to transfect COS cells or other cells that are not responsive to the polypeptides. Transfected cells, which may be cultured on slides are exposed to the labeled polypeptides. The polypeptides can be labeled by a variety of means including iodidation or inclusion of a recognition site for a site-specific protein kinase. Following fixation and incubation, the slides are subjected to autoradiographic analysis. Positive pools are identified and sub-pools are prepared and retransfected using an iterative sub-pooling and rescreening process, eventually yielding a single clones that encodes the putative receptor. As an alternative approach for receptor identification, the labeled polypeptides can be photoaffinity linked with cell membrane or extract preparations that express the receptor molecule. Cross-linked material is resolved by PAGE analysis and exposed to x-ray film. The labeled complex containing the receptors of the polypeptides can be excised, resolved into peptide fragments, and subjected to protein microsequencing. The amino acid sequence obtained from microsequencing would be used to design a set of generate oligonucleotide probes to screen a cDNA library to identify the genes encoding the putative receptors.

This invention provides a method of screening drugs to identify those which enhance (agonists) or block (antagonists) interaction of the polypeptides to their identified receptors. An agonist is a compound which increases the natural biological functions of the polypeptides, while antagonists eliminate such functions. As an example, a mammalian cell or membrane preparation expressing the receptors of the polypeptides would be incubated with a labeled chemokine polypeptide, eg. radioactivity, in the presence of the drug. The ability of the drug to enhance or block this interaction could then be measured.

Potential antagonists include antibodies, or in some cases, oligonucleotides, which bind to the polypeptides. Another example of a potential antagonist is a negative dominant mutant of the polypeptides. Negative dominant mutants are polypeptides which bind to the receptor of the wild-type polypeptide, but fail to retain biological activity.

An assay to detect negative dominant mutants of the polypeptides include an in vitro chemotaxis assay wherein a multiwell chemotaxis chamber equipped with polyvinylpyrrolidone-free polycarbonate membranes is used to measure the chemoattractant ability of the polypeptides for leukocytes in the presence and absence of potential antagonist/inhibitor or agonist molecules.

Antisense constructs prepared using antisense technology are also potential antagonists. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes for the mature polypeptides of the present invention, is used to design an antisense RNA oligonucleotide of from about 10 to 40 base pairs in length. A DNA oligonucleotide is designed to be complementary to a region of the gene involved in transcription (triple-helix, see Lee et al., Nucl. Acids Res., 6:3073 (1979); Cooney et al, Science, 241:456 (1988); and Dervan et al., Science, 251: 1360 (1991)), thereby preventing transcription and the production of the polypeptides. The antisense RNA oligonucleotide hybridizes to the mRNA in vivo and blocks translation of the mRNA molecule into the polypeptides (antisense—Okano, J. Neurochem., 56:560 (1991); Oligodeoxynucleotides as Antisense Inhibitors of Gene Expression, CRC Press, Boca Raton, Fla. (1988)). The oligonucleotides described above can also be delivered to cells such that the antisense RNA or DNA may be expressed in vivo to inhibit production of the polypeptides.

Another potential antagonist is a peptide derivative of the polypeptides which are naturally or synthetically modified analogs of the polypeptides that have lost biological function yet still recognize and bind to the receptors of the polypeptides to thereby effectively block the receptors. Examples of peptide derivatives include, but are not limited to, small peptides or peptide-like molecules.

The antagonists may be employed to inhibit the chemotaxis and activation of macrophages and their precursors, and of neutrophils, basophils, B lymphocytes and some T cell subsets, e.g., activated and CD8+cytotoxic T cells and natural killer cells, in auto-immune and chronic inflammatory and infective diseases. Examples of auto-immune diseases include rheumatoid arthritis, multiple sclerosis, and insulin-dependent diabetes. Some infectious diseases include silicosis, sarcoidosis, idiopathic pulmonary fibrosis by preventing the recruitment and activation of mononuclear phagocytes, idiopathic hyper-eosinophilic syndrome by preventing eosinophil production and migration, endotoxic shock by preventing the migration of macrophages and their production of the chemokine polypeptides of the present invention. The antagonists may also be used for treating atherosclerosis, by preventing monocyte infiltration in the artery wall.

The antagonists may also be used to treat histamine-mediated allergic reactions by inhibiting chemokine-induced mast cell and basophil degranulation and release of histamine.

The antagonists may also be used to treat inflammation by preventing the attraction of monocytes to a wound area. They may also be used to regulate normal pulmonary macrophage populations, since acute and chronic inflammatory pulmonary diseases are associated with sequestration of mononuclear phagocytes in the lung.

Antagonists may also be used to treat rheumatoid arthritis by preventing the attraction of monocytes into synovial fluid in the joints of patients. Monocyte influx and activation plays a significant role in the pathogenesis of both degenerative and inflammatory arthropathies.

The antagonists may be used to interfere with the deleterious cascades attributed primarily to IL-1 and TNF, which prevents the biosynthesis of other inflammatory cytokines. In this way, the antagonists may be used to prevent inflammation. The antagonists may also be used to inhibit prostaglandin-independent fever induced by chemokines.

The antagonists may also be used to treat cases of bone marrow failure, for example, aplastic anemia and myelodysplastic syndrome.

The antagonists may also be used to treat asthma and allergy by preventing eosinophil accumulation in the lung. The antagonists may be employed in a composition with a pharmaceutically acceptable carrier, e.g., as hereinafter described.

The chemokine polypeptides and agonists or antagonists of the present invention may be employed in combination with a suitable pharmaceutical carrier. Such compositions comprise a therapeutically effective amount of the polypeptide, and a pharmaceutically acceptable carrier or excipient. Such a carrier includes but is not limited to saline, buffered saline, dextrose, water, glycerol, ethanol, and combinations thereof. The formulation should suit the mode of administration.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the polypeptides of the present invention may be employed in conjunction with other therapeutic compounds.

The pharmaceutical compositions may be administered in a convenient manner such as by the topical, intravenous, intraperitoneal, intramuscular, intratumor, subcutaneous, intranasal or intradermal routes. The polypeptides are administered in an amount which is effective for treating and/or prophylaxis of the specific indication. In general, the polypeptides will be administered in an amount of at least about 10 $\mu$/kg body weight and in most cases they will be administered in an amount not in excess of about 8 mg/Kg body weight per day. In most cases, the dosage is from about 10 $\mu$g/kg to about 1 mg/kg body weight daily, taking into account the routes of administration, symptoms, etc.

The chemokine polypeptides and agonists or antagonists may be employed in accordance with the present invention by expression of such polypeptides in vivo, which is often referred to as "gene therapy."

Thus, for example, cells from a patient may be engineered with a polynucleotide (DNA or RNA) encoding a polypeptide ex vivo, with the engineered cells then being provided to a patient to be treated with the polypeptide. Such methods are well-known in the art. For example, cells may be engineered by procedures known in the art by use of a retroviral particle containing RNA encoding a polypeptide of the present invention.

Similarly, cells may be engineered in vivo for expression of a polypeptide in vivo by, for example, procedures known in the art. As known in the art, a producer cell for producing a retroviral particle containing RNA encoding the polypeptide of the present invention may be administered to a patient for engineering cells in vivo and expression of the polypeptide in vivo. These and other methods for administering a polypeptide of the present invention by such method should be apparent to those skilled in the art from the teachings of the present invention. For example, the expression vehicle for engineering cells may be other than a retrovirus, for example, an adenovirus which may be used to engineer cells in vivo after combination with a suitable delivery vehicle.

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

Briefly, sequences can be mapped to chromosomes by preparing PCR primers (preferably 15–25 bp) from the cDNA. Computer analysis of the cDNA is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clones to a metaphase chromosomal spread can be used to provide a precise chromosomal location in one step. This technique can be used with cDNA as short as 500 or 600 bases; however, clones larger than 2,000 bp have a higher likelihood of binding to a unique chromosomal location with sufficient signal intensity for simple detection. FISH requires use of the clones from which the EST was derived, and the longer the better. For example, 2,000 bp is good, 4,000 is better, and more than 4,000 is probably not necessary to get good results a reasonable percentage of the time. For a review of this technique, see Verma et al., Human Chromosomes: a Manual of Basic Techniques, Pergamon Press, New York (1988).

Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide.

For preparation of monoclonal antibodies, any technique which provides antibodies produced by continuous cell line cultures can be used. Examples include the hybridoma technique (Kohler and Milstein, 1975, Nature, 256:495–497), the trioma technique, the human B-cell hybridoma technique (Kozbor et al., 1983, Immunology Today 4:72), and the EBV-hybridoma technique to produce human monoclonal antibodies (Cole, et al., 1985, in Monoclonal Antibodies and Cancer Therapy, Alan R. Liss, Inc., pp. 77–96).

Techniques described for the production of single chain antibodies (U.S. Pat. No. 4,946,778) can be adapted to produce single chain antibodies to immunogenic polypeptide products of this invention.

The present invention will be further described with reference to the following examples; however, it is to be understood that the present invention is not limited to such examples. All parts or amounts, unless otherwise specified, are by weight.

In order to facilitate understanding of the following examples certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 μg of plasmid or DNA fragment is used with about 2 units of enzyme in about 20 gl of buffer solution. For the purpose of isolating DNA fragments for plasmid construction, typically 5 to 50 μg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel, D. et al., Nucleic Acids Res., 8:4057 (1980).

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., Id., p. 146). Unless otherwise provided, ligation may be accomplished using known buffers and conditions with 10 units to T4 DNA ligase ("ligase") per 0.5 μg of approximately equimolar amounts of the DNA fragments to be ligated.

Unless otherwise stated, transformation was performed as described in the method of Graham, F. and Van der Eb, A., Virology, 52:456–457 (1973).

EXAMPLE 1

Bacterial Expression and Purification of Ckβ-4

The DNA sequence encoding for Ckβ-4, ATCC #75848, is initially amplified using PCR oligonucleotide primers corresponding to the 5' and 3' sequences of the processed Ckβ-4 protein (minus the putative signal peptide sequence). Additional nucleotides corresponding to Ckβ-4 were added to the 5' and 3' sequences respectively. The 5' oligonucleotide primer has the sequence (SEQ ID No. 5) 5' CCCG-CATGCAAGCAGCAAGCAACTTT 3' contains a SphI restriction enzyme site (bold) followed by 17 nucleotides of Ckβ-4 coding sequence (underlined) starting from the second nucleotide of the sequences coding for the mature protein. The ATG codon is included in the SphI site. In the next codon following the ATG, the first base is from the SphI site and the remaining two bases correspond to the second and third base of the first codon of the putative mature protein. As a consequence, in its construct the amino acids MQA are added at the amino terminus of the mature protein sequence. The 3' sequence, (SEQ ID NO. 6) 5' AAAG-GATCCCATGTTCTTGACTTTTTTACT 3' contains complementary sequences to a BamHl site (bold) and is followed by 21 nucleotides of gene specific sequences preceding the termination codon. The restriction enzyme sites correspond to the restriction enzyme sites on the bacterial expression vector pQE-70 (Qiagen, Inc. 9259 Eton Avenue, Chatsworth, Calif., 91311). pQE-70 encodes antibiotic resistance (Ampr), a bacterial origin of replication (ori), an IPTG-regulatable promoter operator (P/O), a ribosome binding site (RBS), a 6-His tag and restriction enzyme sites. pQE-70 was then digested with SphI and BamHl. The amplified sequences were ligated into pQE-70 and were inserted in frame with the sequence encoding for the histidine tag and the RBS. The ligation mixture was then used to transform the *E. coli* strain available from Qiagen under the trademark M15/rep 4 by the procedure described in Sambrook, J. et al., Molecular Cloning: A Laboratory Manual, Cold Spring Laboratory Press, (1989). M15/rep4 contains multiple copies of the plasmid pREP4, which expresses the laci repressor and also confers kanamycin resistance (Kan'). Transformants are identified by their ability to grow on LB plates and ampicillin/kanamycin resistant colonies were selected. Plasmid DNA was isolated and confirmed by restriction analysis. Clones containing the desired constructs were grown overnight (O/N) in liquid culture in LB media supplemented with both Amp (100 ug/ml) and Kan (25 ug/ml). The O/N culture is used to inoculate a large culture at a ratio of 1:100 to 1:250. The cells were grown to an optical density 600 (O.D.$^{600}$) of between 0.4 and 0.6. IPTG ("Isopropyl-B-D-thiogalacto pyranoside") was then added to a final concentration of 1 mM. IPTG induces by inactivating the laci repressor, clearing the P/O leading to increased gene expression. Cells were grown an extra 3 to 4 hours. Cells were then harvested by centrifugation. The cell pellet was solubilized in the chaotropic agent 6 Molar Guanidine HCl. After clarification, solubilized Ckβ-4 was purified from this solution by chromatography on a Nickel-Chelate column under conditions that allow for tight binding by proteins containing the 6-His tag (Hochuli, E. et al., J. Chromatography 411:177–184 (1984)). CkP-4 (>98% pure) was eluted from the column in 6 molar guanidine HCl pH 5.0. Protein renaturation out of GnHCl can be accomplished by several protocols (Jaenicke, R. and Rudolph, R., Protein Structure—A Practical Approach, IRL Press, New York (1990)). Initially, step dialysis is utilized to remove the GnHCL. Alternatively, the purified protein isolated from the Ni-chelate column can be bound to a second column over which a decreasing linear GnHCL gradient is run. The protein is allowed to renature while bound to the column and is subsequently eluted with a buffer containing 250 mm Imidazole, 150 mM NaCl, 25 mM Tris-HCl pH 7.5 and 10% Glycerol. Finally, soluble protein is dialyzed against a storage buffer containing 5 mM Ammonium Bicarbonate.

EXAMPLE 2

Bacterial Expression and Purification of MCP-4

The cDNA sequence coding for MCP-4 (also referred to as CkP-10), which is present in the human cDNA in the deposit in ATCC No. 75849, is initially amplified using PCR oligonucleotide primers corresponding to the 5' and 3' sequences of the processed MCP-4 protein (minus the signal peptide sequence) and the vector sequences 3' to the MCP-4 gene. Additional nucleotides corresponding to MCP-4 were added to the 5' and 3' sequences respectively. The 5' oligonucleotide primer has the sequence (SEQ ID NO. 7) 5' CCCGCATGCAGCCAGATGCACTCAACG 3' contains a SphI restriction enzyme site (bold) followed by 19 nucleotides of MCP-4 coding sequence (underlined) starting from the sequences coding for the mature protein. The ATG codon is included in the SphI site. The 3' sequence, (SEQ ID NO. 8) 5' AAAGGATCCAGTCTTCAGGGTGTGAGCT 3' contains complementary sequences to a BamH1 site (bold) and is followed by 19 nucleotides of gene specific sequences preceding the termination codon. The restriction enzyme sites correspond to the restriction enzyme sites on the bacterial expression vector pQE-70 (Qiagen, Inc. 9259 Eton Avenue, Chatsworth, Calif., 91311). pQE-70 encodes antibiotic resistance (Amp'), a bacterial origin of replication (ori), an IPTG-regulatable promoter operator (P/O), a ribosome binding site (RBS), a 6-His tag and restriction enzyme sites. pQE-70 was then digested with SphI and BamH1. The amplified sequences were ligated into pQE-70 and were inserted in frame with the sequence encoding for the histidine tag and the RBS. The ligation mixture was then used to transform the *E. coli* strain available from Qiagen under the trademark M15/rep 4 by the procedure described in Sambrook, J. et al., Molecular Cloning: A Laboratory Manual, Cold Spring Laboratory Press, (1989). M15/rep4 contains multiple copies of the plasmid pREP4, which expresses the lacI repressor and also confers kanamycin resistance (Kan'). Transformants are identified by their ability to grow on LB plates and ampicillin/kanamycin resistant colonies were selected. Plasmid DNA was isolated and confirmed by restriction analysis. Clones containing the desired constructs were grown overnight (O/N) in liquid culture in LB media supplemented with both Amp (100 ug/ml) and Kan (25 ug/ml). The O/N culture is used to inoculate a large culture at a ratio of 1:100 to 1:250. The cells were grown to an optical density 600 (O.D.$^{600}$) of between 0.4 and 0.6. IPTG ("Isopropyl-B-D-thiogalacto pyranoside") was then added to a final concentration of 1 mM. IPTG induces by inactivating the laci repressor, clearing the P/O leading to increased gene expression. Cells were grown an extra 3 to 4 hours. Cells were then harvested by centrifugation. The cell pellet was solubilized in the chaotropic agent 6 Molar Guanidine HCl. After clarification, solubilized MCP-4 (also referred to as Ckβ-10) was purified from this solution by chromatography on a Nickel-Chelate column under conditions that allow for tight binding by proteins containing the 6-His tag (Hochuli, E. et al., J. Chromatography 411:177–184 (1984)). MCP-4 (>98% pure) was eluted from the column in 6 molar guanidine HCl pH 5.0. Protein renaturation out of GnHCl can be accomplished by several protocols (Jaenicke, R. and Rudolph, R., Protein Structure—A Practical Approach, IRL Press, New York (1990)). Initially, step dialysis is utilized to remove the GnHCL. Alternatively, the purified protein isolated from the Ni-chelate column can be bound to a second column over which a decreasing linear GnHCL gradient is run. The protein is allowed to renature while bound to the column and is subsequently eluted with a buffer containing 250 mM imidazole, 150 mM NaCl, 25 mM Tris-HCl pH 7.5 and 10% Glycerol. Finally, soluble protein is dialyzed against a storage buffer containing 5 mM Ammonium Bicarbonate. The protein was then analyzed on an SDS-PAGE gel.

EXAMPLE 3

Expression of Recombinant Ckβ-4 in COS cells

The expression of plasmid, Ckβ-4 HA is derived from a vector pcDNAI/Amp (Invitrogen) containing: 1) SV40 origin of replication, 2) ampicillin resistance gene, 3) E. coli replication origin, 4) CMV promoter followed by a polylinker region, a SV40 intron and polyadenylation site. A DNA fragment encoding the entire Ckβ-4 precursor and a HA tag fused in frame to its 3' end was cloned into the polylinker region of the vector, therefore, the recombinant protein expression is directed under the CMV promoter. The HA tag correspond to an epitope derived from the influenza hemagglutinin protein as previously described (I. Wilson, H. Niman, R. Heighten, A Cherenson, M. Connolly, and R. Lerner, 1984, Cell 37, 767). The infusion of HA tag to the target protein allows easy detection of the recombinant protein with an antibody that recognizes the HA epitope.

The plasmid construction strategy is described as follows:

The DNA sequence encoding for Ckβ-4, ATTC Deposit No. 75848, was constructed by PCR on the original EST cloned using two primers: the 5' primer (SEQ ID NO. 9) 5' GGAAAGCTTATGTGCTGTACCAAGAGTTT 3' contains a HindIII site followed by 20 nucleotides of Ckβ-4 coding sequence starting from the initiation codon; the 3' sequence (SEQ ID NO. 10) 5' CGCTCTAGATTAAGCG-TAGTCTGGGACGTCGTATGGGTAACATG-GTTCCTTGACTTTTT 3' contains complementary sequences to XbaI site, translation stop codon, HA tag and the last 20 nucleotides of the Ckβ-4 coding sequence (not including the stop codon). Therefore, the PCR product contains a HindIII site, Ckβ-4 coding sequence followed by HA tag fused in frame, a translation termination stop codon next to the HA tag, and an XbaI site. The PCR amplified DNA fragment and the vector, pcDNAI/Amp, were digested with HindIII and XbaI restriction enzyme and ligated. The ligation mixture was transformed into E. coli strain SURE (available from Stratagene Cloning Systems, 11099 North Torrey Pines Road, La Jolla, Calif. 92037) the transformed culture was plated on ampicillin media plates and resistant colonies were selected. Plasmid DNA was isolated from transformants and examined by restriction analysis for the presence of the correct fragment. For expression of the recombinant Ckβ-4, COS cells were transfected with the expression vector by DEAE-DEXTRAN method. (J. Sambrook, E. Fritsch, T. Maniatis, Molecular Cloning: A Laboratory Manual, Cold Spring Laboratory Press, (1989)). The expression of the Ckβ-4 HA protein was detected by radiolabelling and immunoprecipitation method. (E. Harlow, D. Lane, Antibodies: A Laboratory Manual, Cold Spring Harbor Laboratory Press, (1988)). Cells were labelled for 8 hours with $^{35}$S-cysteine two days post transfection. Culture media were then collected and cells were lysed with detergent (RIPA buffer (150 mM NaCl, 1% NP-40, 0.1% SDS, 50mM Tris, pH 7.5). (Wilson, I. et al., Id. 37:767 (1984)). both cell lysate and culture media were precipitated with a HA specific monoclonal antibody. Proteins precipitated were analyzed by SDS-PAGE.

EXAMPLE 4

Expression of Recombinant MCP-4 in COS cells

The expression of plasmid, MCP-4-HA (also referred to as Ckβ-10 HA) is derived from a vector pcDNAI/Amp (Invitrogen) containing: 1) SV40 origin of replication, 2) ampicillin resistance gene, 3) E. coli replication origin, 4) CMV promoter followed by a polylinker region, a SV40 intron and polyadenylation site. A DNA fragment encoding the entire MCP-4 precursor and a HA tag fused in frame to its 3' end was cloned into the polylinker region of the vector, therefore, the recombinant protein expression is directed under the CMV promoter. The HA tag correspond to an epitope derived from the influenza hemagglutinin protein as previously described (I. Wilson, H. Niman, R. Heighten, A Cherenson, M. Connolly, and R. Lerner, 1984, Cell 37, 767). The infusion of HA tag to the target protein allows easy detection of the recombinant protein with an antibody that recognizes the HA epitope.

The plasmid construction strategy is described as follows:

The cDNA sequence encoding for MCP-4 (also referred to as Ckβ-10), which is present in the cDNA insert in the DNA in ATTC. Deposit No. 75849, was constructed by PCR on the original EST cloned using two primers: the 5' primer (SEQ ID NO. 11) 5' GGAAAGCTTATGAAAGTTTCTG-CAGTGC 3' contains a HindIII site followed by 19 nucleotides of MCP-4 coding sequence starting from the initiation codon; the 3' sequence (SEQ ID NO. 12): 5'-CGCTCTAGAT CAAGCGTAGT CTGGGACGTC GTATGGGTAA GTCT-TCAGGG TGTGAGCT-3' contains complementary sequences to XbaI site, translation stop codon, HA tag and the last 19 nucleotides of the MCP-4 coding sequence (not including the stop codon). Therefore, the PCR product contains a HindIII site, MCP-4 coding sequence followed by HA tag fused in frame, a translation termination stop codon next to the HA tag, and an XbaI site. The PCR amplified DNA fragment and the vector, pcDNAI/Amp, were digested with HindIII and BamH1 restriction enzyme and ligated. The ligation mixture was transformed into E. coli strain SURE (available from Stratagene Cloning Systems, 11099 North Torrey Pines Road, La Jolla, Calif. 92037) the transformed culture was plated on ampicillin media plates and resistant colonies were selected. Plasmid DNA was isolated from transformants and examined by restriction analysis for the presence of the correct fragment. For expression of the recombinant MCP-4 (also known as Ckβ-10), COS cells were transfected with the expression vector by DEAE-DEXTRAN method. (J. Sambrook, E. Fritsch, T. Maniatis, Molecular Cloning: A Laboratory Manual, Cold Spring Laboratory Press, (1989)). The expression of the MCP-4-HA protein was detected by radiolabelling and immunoprecipitation method. (E. Harlow, D. Lane, Antibodies: A Laboratory Manual, Cold Spring Harbor Laboratory Press, (1988)). Cells were labelled for 8 hours with $^{35}$S-cysteine two days post transfection. Culture media were then collected and cells were lysed with detergent (RIPA buffer (150 mM NaCl, 1% NP-40, 0.1% SDS, 0.5% DOC, 50 mM Tris, pH 7.5). (Wilson, I. et al., Id. 37:767 (1984)). Both cell lysate and culture media were precipitated with a HA specific monoclonal antibody. Proteins precipitated were analyzed by SDS-PAGE.

EXAMPLE 5

Further cloning and expression of MCP-4 using the baculovirus expression system

The cDNA sequence encoding the full length MCP-4 protein (also known as Ckβ-10 protein), in the DNA in ATCC Deposit No. 75849, was amplified using PCR oligonucleotide primers corresponding to the 5' and 3' sequences of the gene, as follows.

The 5' primer has the sequence (SEQ ID NO. 13): 5'-CGCGGGATCC TTAACCTTCA ACATGAAA-3' and contains a BamHI restriction enzyme site (in bold) followed by 12 nucleotides resembling an efficient signal for the initiation of translation in eukaryotic cells (J. Mol. Biol. 1987, 196, 947–950, Kozak, M.), and then is the first 6 nucleotides of the MCP-4 coding sequence (the initiation codon for translation "ATG" is underlined).

The 3' primer has the sequence (SEQ ID NO. 14): 5'-CGCGGGTACC TTAACACATA GTACATTTT-3' and contains the cleavage site for the restriction endonuclease Asp781 and 19 nucleotides complementary to the 3' non-translated sequence of the MCP-4 gene. The amplified sequences were isolated from a 1% agarose gel using a commercially available kit ("Geneclean," BIO 101 Inc., La Jolla, Calif.). The fragment was then digested with the endonucleases BamHI and Asp781 and then purified again on a 1% agarose gel. This fragment is designated F2.

The vector pA2 (modification of pVL941 vector, discussed below) is used for the expression of the MCP-4 protein using the baculovirus expression system (for review see: Summers, M. D. and Smith, G. E. 1987, A manual of methods for baculovirus vectors and insect cell culture procedures, Texas Agricultural Experimental Station Bulletin No. 1555). This expression vector contains the strong polyhedrin promoter of the Autographa californica nuclear polyhedrosis virus (AcMNPV) followed by the recognition sites for the restriction endonucleases BamHI and Asp781. The polyadenylation site of the simian virus (SV)40 is used for efficient polyadenylation. For an easy selection of recombinant viruses the beta-galactosidase gene from E.coli is inserted in the same orientation as the polyhedrin promoter followed by the polyadenylation signal of the polyhedrin gene. The polyhedrin sequences are flanked at both sides by viral sequences for the cell-mediated homologous recombination of cotransfected wild-type viral DNA. Many other baculovirus vectors could be used in place of pRG1 such as pAc373, pVL941 and pAcIM1 (Luckow, V. A. and Summers, M. D., Virology, 170:31–39).

The plasmid was digested with the restriction enzymes BamHI and Asp781 and then dephosphorylated using calf intestinal phosphatase by procedures known in the art. The DNA was then isolated from a 1% agarose gel. This vector DNA is designated V2.

Fragment F2 and the dephosphorylated plasmid V2 were ligated with T4 DNA ligase. $^{E.\ coli}$ HB101 cells were then transformed and bacteria identified that contained the plasmid pBacMCP-4 (also known as pBacCkβ-10) with the MCP-4 gene using the enzymes BamHI and Asp781. The sequence of the cloned fragment was confirmed by DNA sequencing.

5 μg of the plasmid pBacMCP-4 were cotransfected with 1.0 μg of a commercially available linearized baculovirus ("BaculoGold™ baculovirus DNA", Pharmingen, San Diego, Calif.) using the lipofection method (Felgner et al. Proc. Natl. Acad. Sci. USA, 84:7413–7417 (1987)).

1 μg of BaculoGold™ virus DNA and 5 μg of the plasmid pBacMCP-4 were mixed in a sterile well of a microtiter plate containing 50 μl of serum free Grace's medium (Life Technologies Inc., Gaithersburg, Md.). Afterwards 10 μl Lipofectin plus 90 μl Grace's medium were added, mixed and incubated for 15 minutes at room temperature. Then the transfection mixture was added dropwise to the Sf9 insect cells (ATCC CRL 1711) seeded in a 35 mm tissue culture plate with 1 ml Grace' medium without serum. The plate was rocked back and forth to mix the newly added solution. The plate was then incubated for 5 hours at 27° C. After 5 hours the transfection solution was removed from the plate and 1 ml of Grace's insect medium supplemented with 10% fetal calf serum was added. The plate was put back into an incubator and cultivation continued at 27° C. for four days.

After four days the supernatant was collected and a plaque assay performed similar as described by Summers and Smith (supra). As a modification an agarose gel with "Blue Gal" (Life Technologies Inc., Gaithersburg) was used which allows an easy isolation of blue stained plaques. (A detailed description of a "plaque assay" can also be found in the user's guide for insect cell culture and baculovirology distributed by Life Technologies Inc., Gaithersburg, page 9–10).

Four days after the serial dilution of the viruses was added to the cells, blue stained plaques were picked with the tip of an Eppendorf pipette. The agar containing the recombinant viruses was then resuspended in an Eppendorf tube containing 200 μl of Grace's medium. The agar was removed by a brief centrifugation and the supernatant containing the recombinant baculoviruses was used to infect Sf9 cells seeded in 35 mm dishes. Four days later the supernatants of these culture dishes were harvested and then stored at 4° C.

Sf9 cells were grown in Grace's medium supplemented with 10% heat-inactivated FBS. The cells were infected with the recombinant baculovirus V-MCP-4 (also referred to as V-Ckβ-10) at a multiplicity of infection (MOI) of 2. Six hours later the medium was removed and replaced with SF900 II medium minus methionine and cysteine (Life Technologies Inc., Gaithersburg). 42 hours later 5 μCi of $^{35}$S-methionine and 5 μCi $^{35}$S cysteine (Amersham) were added. The cells were further incubated for 16 hours before they were harvested by centrifugation and the labelled proteins visualized by SDS-PAGE and autoradiography.

EXAMPLES 6 THROUGH 12

Expression of MCP-4 (also referred to as Ckβ-10) Using a Baculovirus Expression System and a Drosophila Cell Expression System and Characterization of the Expressed MCP-4

The following examples 6–12 were carried out as described above, with the modifications and additional techniques described generally immediately below, as well as in the specific examples themselves. (As noted elsewhere herein MCP-4 also is referred to and known as Ckβ-10.)

Cloning and Expression

The full-length cDNA encoding MCP-4 was cloned into a baculovirus expression vector (PharMingen), SF9 cells were infected with the recombinant baculovirus according to the manufacturer's instructions, and the cell supernatant was collected by low-speed centrifugation. The supernatant was treated with a cocktail of protease inhibitors (20 ug/ml pefabloc SC, 1 ug/ml leupeptin, 1 ug/ml E64 and 1 mM EDTA), and the recombinant protein was purified by heparin affinity, cation exchange, and size exclusion chromatography. The protein of over 95% purity was analyzed by electron spray mass spectrometry and sequenced.

Chemokines

The chemokines used for comparison, MCP-1, MCP-2, MCP-3, RANTES, MIP-1α and eotaxin, were chemically synthesized according to established protocols Clark-Lewis et al., Biochemistry 30:3128–3135 (1991).

Cells

Monocytes (Uguccioni et al., Eur. J. Immunol. 25: 64–68 (1995)), and neutrophils (Peveri et al., J. Exp. Med. 167:1547–1559 (1988)), were isolated at more than 90 percent purity from donor blood buffy coats supplied by the Central Laboratory of the Swiss Red Cross. The same source was used for the isolation of blood lymphocytes (Loetscher et al., FASEB J. 8:1055–1060 (1994). Human CD4+ and CD8+ T cell clones were maintained in culture and used according to Loetscher et al., FASEB J. 8:1055–1060 (1994). Fresh blood of healthy individuals was used to purify eosinophils by dextran sedimentation followed by Percoll density-gradient centrifucation and negative selection with anti-CD16 mAB-coated magnetic beads (Rot et al., Exp. Med. 179:8960–8964 (1995)).

EXAMPLE 6

Expression of MCP-4 (also referred to as Ckβ-10) in a Baculovirus Expression System Construction of a Baculovirus Transfer Vector Containing the Coding Sequence of MCP4

The expression vector for this example was made much as described above. The plasmid vector pA2 was used to express MCP-4. This plasmid is a derivative of pNR704, described by Gentz et al., Eur. J. Biochem 210 :545–554 (1992). The *E coli* β-galactosidase gene has been introduced into the vector as well to facilitate selection of recombinants.

The following PCR oligonucleotides were used to isolate and amplify the coding sequence of MCP-4. forward primer (SEQ ID NO. 15): 5' GCG GGATCCTTAACCTTCAACATGAAA reverse primer (SEQ ID NO. 16) 5' CGCG GGTACCTTAACACATAGTACATTTT After amplification the fragment was digested with the restriction enzymes BamHI and Asp718 and then inserted into the expression vector, which contains these restriction sites downstream of the polyhedron promoter.

Proper insertion and orientation of vector and insert was confirmed by restriction analysis and DNA sequencing.

Isolation of Recombinant Baculovirus 5 ug of the expression vector containing the MCP-4 cDNA and 1 ug of linearized baculovirus DNA ("BaculoGOLD TM, Pharmingen, San Diego, Calif.) were contransfected into Sf9 cells using the lipofectin method. After 3–4 days supernatants were collected. A series of limited dilutions was then performed and single, blue stained plaques were isolated.

The insect cell line Sf9 used in this example is well known and readily available. It may be obtained, for example, from the American type culture collection: ATCC CRL 1711, among other places.

Purification of MCP-4

Sf9 cells were grown at 27° C. en EX-CELL 400 medium containing 2% FBS. Before infection the cells were collected by low-speed centrifugation and the medium was replaced by EX-CELL 400 medium without serum. After 6 hours the cells were infected at an MOI=2. About 72 hours after infection the cells were removed by low-speed centrifugation. The supernatant was treated with a cocktail of protease inhibitors (20 ugml pefabloc SC, 1 ug/ml leupeptin, 1 ug/ml E-64 and 1 mM EDTA). The supernatant was passed through a strong cation exchange column I poros 50 HS, (Perseptive Biosystem) for initial capturing. The recombinant MCP-4 protein was eluted with 1 M NaCl in 25 mM sodium acetate, pH 6 and then further purified by heparin affinity chromatography (poros 20 HEI1, Perseptive Biosystem). The resultant MCP-4 protein was polished by size exclusion chromatography (Sephacryl S200 HR, Pharmacia). The purified MCP-4 obtained following size exclusion was about 95% or more pure. This material was further analyzed by mass spectroscopy and by microsequencing.

The purified material was analysed by standard mass spectral analysis.

The purified MCP-4 also was analysed by microsequencing, using well known and routine techniques. For this purpose, the purified material was applied to SDS polyacrylamide gel electrophoresis (Novex 4–20% gels) and transblotted onto a ProBlott membrane (Applied Biosystems, Inc. (ABI). After staining with Ponceau S (0.2% in 4% acetic acid) the protein band was excised, placed in a "Blot Cartridge" and then subjected to N-terminal amino acid sequence analysis using a model ABI-494 sequencer (Perking-Elmer-Applied Biosystems, Inc.) with the Gasphase Blot cycler.

Analytical Results

Expression of MCP-4 from cloned genes using a baculovirus expression system yielded several forms of MCP-4.

MCP-4 made by expressing cDNA of FIG. 1 in a baculovirus expression system, isolated and characterized by electrophoresis on SDS PAGE containing 18% urea (Padrines et al., FEBS Lett. 352:231–235 (1994), as described above, gave rise to a single, somewhat broad band with an apparent $M_r$ around 8,000 dalton. There was no indication of contaminant proteins.

Mass spectrometry of the purified preparation yielded two main components with masses of 8,576 and 8,754 daltons, respectively.

Microsequencing revealed that three mature forms of MCP-4, which differ in length by a few residues at the $NH_2$ terminus.

The sequences of these MCP-4 polypeptides are shown in FIG. 5, along with the amino acid sequence encoded in the full length cDNA, which is also shown aligned with the sequences of MCP-3 and eotaxin. The major form of MCP-4 shares 60% amino acid identity with these proteins, and has 29, 39 and 41% identity with RANTES, MIP-1α and MIP-1β.

A mixture of the two closely related variants was used for the activity assays described herein below.

EXAMPLE 7

MCP-4 Stimulates Chemotaxis of a Variety of Blood Cells

Chemotaxis was assessed in 48-well chambers (Neuro Probe, Cabin John, MD, USA) using polyvinylprrolidone-free polycarbonate membranes (Nucleopore) with 5 um pores for monocytes and eosinophils, and 3-um pores for lymphocytes, RPMI 1640 supplemented with 20 mM hepes, pH 7.4, and 1% pasteurized plasma protein solution (5% PPL SRK; Swiss Red Cross Laboratory, Bern, Switzerland) was used to dissolve the chemokines, which were placed in the lower well, and to suspend the cells (50,000 monocytes or eosinophils and 100,000 lymphocytes per upper well). After 60 min at 37° C., the membrane was removed, washed on the upper side with PBS, fixed and stained. All assays were done in triplicate, and the migrated cells were counted in five randomly selected fields at 1,000-fold magnification. Spontaneous migration was determined in the absence of chemoaltractant.

Figure 6B:
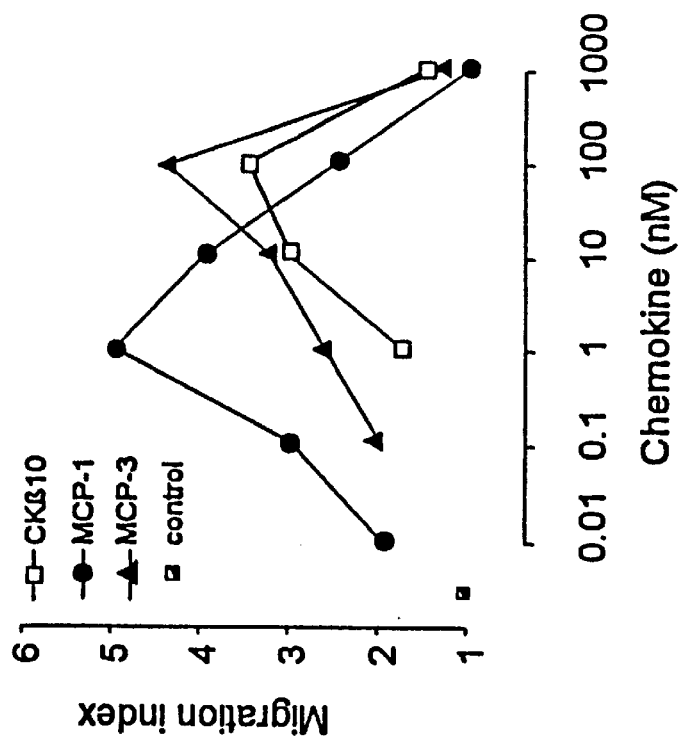
FIG. 6 is a pair of graphs showing (A) release of N-acetyl-β-D-glucosaminidase from cytochalasin B-treated human blood monocytes in response to MCP-4 (Ckβ-10), Eotaxin, MCP-1, MCP-2, MCP-3 and RANTES, and (B) migration index of cytochalasin B-treated monocytes in response to MCP-4 (Ckβ-10), MCP-1, MCP-3 and a negative control.
Figure 6A:
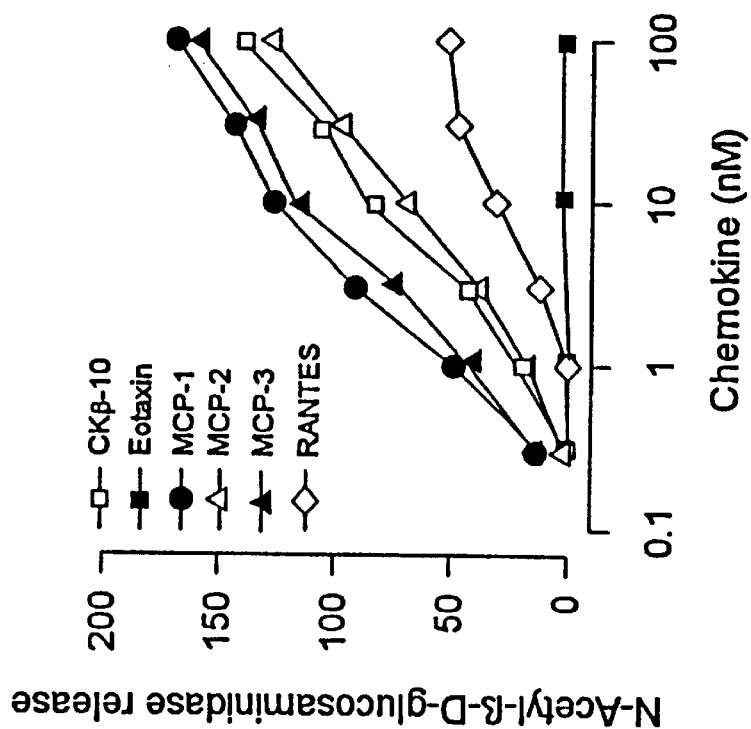

MCP-4 induced the migration of monocytes, eosinophils and lymphocytes with a typical bimodal concentration dependence (as shown in FIGS. 6. 7 and 8).

The activity on monocytes was comparable to that of MCP-3, both in terms of efficacy and potency, as indicated by the numbers of migrating cells and the concentration (100 nM) at which maximum effects were observed, as illustrated in Graph (B) in FIG. 6. In agreement with a former study (Uguccioni et al., Eur. J. Immunol. 25:64–68 (1995) MCP-1 was somewhat more efficacious and considerably more potent on these cells, reaching maximum effect at 1 nM.

MCP-4 also induced strong migration of CD4+ and CD8+ T lymphocytes, as illustrated in FIG. 7. Its efficacy was similar to that of MCP-1, but 10 to 100 nM MCP-4 were required for the maximum effects as compared to 1 nM MCP-1. Some migration of both types of T cells was also observed with eotaxin at concentrations between 10 nM and 1 uM. Freshly prepared blood lymphocytes did not migrate in response to any of the chemokines that were effective on cloned cells.

On eosinophils, as illustrated in FIG. 8, MCP-4 elicited migration similar to eotaxin, with a maximum at 10 to 30 nM. MCP-3 had comparable efficacy, but its maximum effective concentration was 100 nM. Eotaxin and MCP-3 both potent attractants for these cells. MCP-1 is not a chemoattractant for eosinophils and served as negative control.

EXAMPLE 8

MCP-4 (also referred to as Ckβ-10) Stimulates Cells to Release of N-acetyl-β-D-glucosaminidase Uguccioni et al., Eur. J. Immunol. 25:64–68 (1995) showed that measuring the release of N-acetyl-β-D-glucosaminidase in response to chemostimulation is a particularly reliable and convenient way to determine quantitatively the response of monocytes. Monocyte responsiveness to chemokines was determined exactly as described therein.

In brief, samples of $1.2 \times 10^6$ monocytes in 0.3 ml prewarmed medium (136 mM NaCl, 4.8 mM KCl, 1.2 mM $KH_2PO_4$, 1 mM $CaCl_2$, 20 mM Hepes, pH 7.4, 5 mM D-glucose and 1 mg/ml fatty acid-free BSA) were pretreated for 2 min with cytochalasin B (2.7 ug/ml) and stimulated with a chemokine. The reaction was stopped after 3 min by cooling on ice and centrifugation (6,000, 3 min), and enzyme activity was determined in the supernatant.

As shown in FIG. 6, Graph (A), cells exposed to MCP-4 were stimulated to release abundant amounts of lysosomal enzymes such as N-acetyl-β-D-glucosaminidase. In this regard, MCP-4 was as potent as MCP-2 and similar to the effects of other monocyte chemotactic proteins. In contrast, RANTES stimulated considerably less enzyme release and there was no stimulation of release by eotaxin.

Similarly, elastase release by neutrophils was measured to determine responsiveness to chemokines, in accordance with the methods described in Peveri et al., J. Exp. Med. 167:1547–1559 (1988). MCP-4 did not stimulate elastase release by neutrophils in these experiments.

EXAMPLE 9

MCP-4 (also referred to as Ckβ-10) Modulates Cytostolic Free $Ca^{2+}$

Changes in the cytosolic free $Ca^{2+}$ concentration. ($[Ca^{2+}]$) were measured in monocytes, eosinophils and lymphocytes, using standard techniques, essentially as described by von Tscharner et al., Nature 324:369–372 (1986).

Cells were loaded with fura-2 by incubation for 30 min at 37° with 0.2 nmol fura-2 acetoxymethylester per $10^6$ cells in a buffer containing 136 mM NaCl, 4.8 mM KCl, 1 mM $CaCl_2$, 5 mM glucose, and 20 mM HEPES, pH 7.4. After centrifugation, the fura-loaded cells were resuspended in the same buffer ($10^6$ cells/ml) and stimulated with chemokine at 37° C. [$CaCl_2$]-related fluorescence changes then were recorded.

A rapid and transient rise in [$Ca^2+$] was observed after MCP-4 stimulation of monocytes, lymphocytes and eosinophils. The rate and magnitude of the rise increased with the MCP-4 concentration. Maximum rises in [Ca2+] were obtained at concentrations between 10 to 100 nM. MCP-4 and MCP-1 exhibited similar concentration-dependent [$Ca^{2+}$] transient induction on both CD4+ and CD8+ T lymphocytes. MIP-1α and eotaxin induced much smaller, but significant, [Ca2+] changes in both types of cells. The lower potency of these cytokines in this regard is consistent with previous reports by Loetscher et al., FASEB J. 8:1055–1060 (1994) and others that they are weak lymphocyte attractants.

EXAMPLE 10

Receptor Usage/Desensitization Experiments

Receptor usage was tested by monitoring changes in [Ca2+] brought about by repeated chemokine stimulation at short intervals. The consequent desensitization of the exposure regimen provides a measure of receptor utilization. The determinations were made using 90 sec intervals exactly as described for monocytes by Uguccioni et al., Eur. J. Immunol. 25:64–68 (1995). Determinations were made in monocytes and eosinophils.

Stimulation of monocytes with MCP-1 or MCP-3 abolished responsiveness to MCP-4, indicating that the novel chemokine shares receptors with these monocyte chemotactic proteins. In contrast, stimulation with RANTES or MIP-1α did not affect MCP-4 responsiveness in this assay.

In tests of the opposite polarity, monocytes first stimulated with MCP-4 were markedly less responsive to MCP-1, RANTES and MIP-1α and slightly less responsive to MCP-3. Densensitization increased with the concentration of MCP-4

The results also show that MCP-4 shares receptors with other monocyte chemotactic proteins and that MCP-4 recognizes a receptor that binds RANTES and MIP-1α, In eosinophils, MCP-4 exhibited marked crossdesensitization with MCP-3, RANTES and eotaxin. In fact, it abrogated the response to subsequent stimulation by eotaxin and MCP-3, markedly decreased responsiveness to RANTES. MCP-4, and it therefore appears to be a major agonist for these cells. The results indicate that MCP-4 shares receptors with MCP-3, RANTES and Eotaxin.

In contrast, stimulation with MCP-4 did not affect the response of eosinophils to MIP-1α. Thus, MIP-1α. receptors apparently do not recognize or bind MCP-4. The same receptor is likely to bind RANTES, which retained some activity on cells that had been stimulated with MCP-4.

EXAMPLE 11

Expression of MCP-4 (also referred to as Ckβ-10) in a Drosophila Expression System A full-length cDNA encoding MCP-4 was expressed in a well known and readily available drosophila cell expression, using routine techniques for expressing cloned genes in this system.

Expressed MCP-4 was prepared from cells in which the cDNA was expressed and then characterized, using well known, routine techniques for characterizing polypeptides and proteins.

Several forms of MCP-4 was found in the expressing cells, including MCP-4 with shortened amino and carboxyl termini and MCP-4 comprising post-translational modifications.

In particular, drosophila cells expressed MCP-4 having the amino acid sequence set out in FIG. 1 except for the following differences.

N-tterminal sequences changed to:

Dro1:QGLKAQPD

Dro2:pyroQGLKAQPD

Dro3++: LNVPST, which occurred in three forms differing by different deletions of the C-terminal sequence. In particular DRO3 was found with T, T (des3) and A (des 5) carboxyl termini as indicated in FIG. 5.

The full sequences are set out in FIG. 5.

EXAMPLE 12

Assay of MCP-4 (also referred to as Ckβ-10) Produced in a Drosophila Expression System Differing forms of MCP-4 expressed in drosophila cells were assays for activities using the techniques described herein above.

Dro1 and Dro2 mobilized monocyte, PBL and EOL-3 cells in the chemotaxis assays, and they both were active in Ca2+ mobilization assays.

Dro3 showed substantially reduced bioactivity and, in fact, can be used as an antagonist.

EXAMPLE 13

CKD-4 Enhances Survival of Cortical Neurons

Cortical cells were derived from rat fetuses at gestation day 17. Following the preparation of a single cell suspension, the cells were plated at a density of 15,000 cells/well in serum containing medium. After 24 hr. the medium was changed to a serum-free medium and the test factors were added. The medium was changed every other day and the test factors were added again.

After 6–7 days the cell viability was determined using a two-color fluorescence that provides simultaneous determination of live and dead cells. Live cells in this assay are determined by intracellular esterase activity, quantitated by conversion of cell-permeant calcein AM, which is nearly non-fluorescent, calcein, which is intensely fluorescent. Living cells almost universally express esterase activity and well the polycationic, fluorescent calcein. Thus, living cells produce a uniform, intense green fluorescence in the assay. The assay can be calibrated so that emission at 520 nm can be used to determine total viable cell number in cultures. The assay can be implemented, as it was for the present example, using the Live/Dead Cell Assay Kit commercially available from Molecular Probes.

As shown in FIG. 9, CKβ-4 (closed squares) stimulates cortical neuron cell survival in culture similarly to HG0100 (open squares).

Each point represents the average for six replicate cultures.

EXAMPLE 14

CKP-4 Increases Outgrowth of Cortical Neurons

Cultures of cortical neurons were prepared and maintained according to standard techniques. After 6 to 7 days in the presence of the test factors, the amount of neurofilament protein present in the cultures was determined by ELISA.

As shown in FIG. 10, CKβ-4 at concentrations of 10–100 ng/ml enhances neurite outgrowth similarly to bFGF-10. Results are for six replicate cultures.

EXAMPLE 15

CKO-4 Induces Chemotaxis of Peripheral Blood Lymphocytes

Chemotaxis of peripheral blood lymphocytes in response to Ckβ-4 and MCP-1 was determined by the above described methods.

As shown in FIG. 11, Ckβ-4 exhibit a peak of activity at 1 to 10 ng/ml, comparable to the activity of MCP-1 at saturation.

Numerous modifications and variations of the present invention are possible in light of the above teachings and, therefore, within the scope of the appended claims, the invention may be practiced otherwise than as particularly described.

---

What is claimed is:

1. An isolated polypeptide comprising an amino acid sequence selected from the group consisting of:
   (a) at least 30 contiguous amino acid residues of SEQ ID NO:2; and
   (b) at least 30 contiguous amino acid residues of the mature protein encoded by the human cDNA contained in ATCC Deposit No. 75848.

2. The isolated polypeptide of claim 1 wherein said amino acid sequence is (a).

3. The isolated polypeptide of claim 1 wherein said amino acid sequence is (b).

4. The isolated polypeptide of claim 2 comprising at least 50 contiguous amino acid residues of SEQ ID NO:2.

5. The isolated polypeptide of claim 4 comprising the amino acid sequence shown as residues 27 to 96 of SEQ ID NO:2.

6. The isolated polypeptide of claim 5 comprising the amino acid sequence shown as residues 2 to 96 of SEQ ID NO:2.

7. The isolated polypeptide of claim 6 comprising the amino acid sequence shown as residues 1 to 96 of SEQ ID NO:2.

8. The isolated polypeptide of claim 1 comprising at least 50 contiguous amino acid residues of the mature protein encoded by the human cDNA contained in ATCC Deposit No. 75848.

9. The isolated polypeptide of claim 8 comprising the amino acid sequence of a mature protein encoded by the human cDNA contained in ATCC Deposit No. 75848.

10. The isolated polypeptide of claim 9 comprising the amino acid sequence of the proprotein encoded by the human cDNA contained in ATCC Deposit No. 75848.

11. The isolated polypeptide of claim 1 fused to a heterologous polypeptide.

12. A composition comprising the isolated polypeptide of claim 1 in a pharmaceutically acceptable carrier.

13. An isolated polypeptide comprising an amino acid sequence selected from the group consisting of:
   (a) at least 30 contiguous amino acid residues of SEQ ID NO:4; and
   (b) at least 30 contiguous amino acid residues of the mature polypeptide encoded by the human cDNA contained in ATCC Deposit No. 75849.

14. The isolated polypeptide of claim 13 wherein said amino acid sequence is (a).

15. The isolated polypeptide of claim 13 wherein said amino acid sequence is (b).

16. The isolated polypeptide of claim 13 comprising at least 50 contiguous amino acid residues of SEQ ID NO:4.

17. The isolated polypeptide of claim, 16 consisting of the amino acid sequence shown as residues 28–93 in SEQ ID NO:4.

18. The isolated polypeptide of claim 16 consisting of the amino acid sequence shown as residues 28–95 in SEQ ID NO:4.

19. The isolated polypeptide of claim 16 consisting of the amino acid sequence shown as residues 28–98 in SEQ ID NO:4.

20. The isolated polypeptide of claim 16 comprising the amino acid sequence shown as residues 24–98 in SEQ ID NO:4.

21. The isolated polypeptide of claim 20 comprising the amino acid sequence shown as residues 22–98 in SEQ ID NO:4.

22. The isolated polypeptide of claim 21 consisting of the amino acid sequence shown as residues 20–98 in SEQ ID NO:4.

23. The isolated polypeptide of claim 20 comprising the amino acid sequence shown as residues 17–98 in SEQ ID NO:4.

24. The isolated polypeptide of claim 23 comprising the amino acid sequence shown as residues 2–98 in SEQ ID NO:4.

25. The isolated polypeptide of claim 24 comprising the amino acid sequence shown as residues 1–98 in SEQ ID NO:4.

26. The isolated polypeptide of claim 13 comprising at least 50 contiguous amino acid residues of the mature protein encoded by the human cDNA contained in ATCC Deposit No. 75849.

27. The isolated polypeptide of claim 26 comprising the amino acid sequence of a mature polypeptide encoded by the human cDNA contained in ATCC Deposit No. 75849.

28. The isolated polypeptide of claim 27 comprising the amino acid sequence of the proprotein encoded by the human cDNA contained in ATCC Deposit No. 75849.

29. The isolated polypeptide of claim 1 fused to a heterologous polypeptide.

30. A composition comprising the isolated polypeptide of claim 1 in a pharmaceutically acceptable carrier.

* * * * *

SEQUENCE LISTING (1) GENERAL INFORMATION:

(iii) NUMBER OF SEQUENCES: 20

(2) INFORMATION FOR SEQ ID NO:1:

(i) SEQUENCE CHARACTERISTICS:
      (A) LENGTH: 291 base pairs
      (B) TYPE: nucleic acid
      (C) STRANDEDNESS: single
      (D) TOPOLOGY: linear (ii) MOLECULE TYPE: DNA (genomic)

```
    (ix) FEATURE:
         (A) NAME/KEY: CDS
         (B) LOCATION: 1..288

(xi) SEQUENCE DESCRIPTION: SEQ ID NO:1:

ATG TGC TGT ACC AAG AGT TTG CTC CTG GCT GCT TTG ATG TCA GTG CTG        48
Met Cys Cys Thr Lys Ser Leu Leu Leu Ala Ala Leu Met Ser Val Leu
 1               5                  10                  15

CTA CTC CAC CTC TGC GGC GAA TCA GAA GCA GCA AGC AAC TTT GAC TGC        96
Leu Leu His Leu Cys Gly Glu Ser Glu Ala Ala Ser Asn Phe Asp Cys
                20                  25                  30

TGT CTT GGA TAC ACA GAC CGT ATT CTT CAT CCT AAA TTT ATT GTG GGC       144
Cys Leu Gly Tyr Thr Asp Arg Ile Leu His Pro Lys Phe Ile Val Gly
        35                  40                  45

TTC ACA CGG CAG CTG GCC AAT GAA GGC TGT GAC ATC AAT GCT ATC ATC       192
Phe Thr Arg Gln Leu Ala Asn Glu Gly Cys Asp Ile Asn Ala Ile Ile
50                  55                  60

TTT CAC ACA AAG AAA AAG TTG TCT GTG TGC GCA AAT CCA AAA CAG ACT       240
Phe His Thr Lys Lys Lys Leu Ser Val Cys Ala Asn Pro Lys Gln Thr
65                  70                  75                  80

TGG GTG AAA TAT ATT GTG CGT CTC CTC AGT AAA AAA GTC AAG AAC ATG       288
Trp Val Lys Tyr Ile Val Arg Leu Leu Ser Lys Lys Val Lys Asn Met
                85                  90                  95

TAA                                                                    291

(2) INFORMATION FOR SEQ ID NO:2:

(i) SEQUENCE CHARACTERISTICS:
          (A) LENGTH: 96 amino acids
          (B) TYPE: amino acid
          (D) TOPOLOGY: linear (ii) MOLECULE TYPE: protein (xi) SEQUENCE DESCRIPTION: SEQ ID NO:2:

Met Cys Cys Thr Lys Ser Leu Leu Leu Ala Ala Leu Met Ser Val Leu
 1               5                  10                  15

Leu Leu His Leu Cys Gly Glu Ser Glu Ala Ala Ser Asn Phe Asp Cys
                20                  25                  30

Cys Leu Gly Tyr Thr Asp Arg Ile Leu His Pro Lys Phe Ile Val Gly
        35                  40                  45

Phe Thr Arg Gln Leu Ala Asn Glu Gly Cys Asp Ile Asn Ala Ile Ile
    50                  55                  60

Phe His Thr Lys Lys Lys Leu Ser Val Cys Ala Asn Pro Lys Gln Thr
65                  70                  75                  80

Trp Val Lys Tyr Ile Val Arg Leu Leu Ser Lys Lys Val Lys Asn Met
                85                  90                  95

(2) INFORMATION FOR SEQ ID NO:3:

(i) SEQUENCE CHARACTERISTICS:
          (A) LENGTH: 297 base pairs
          (B) TYPE: nucleic acid
          (C) STRANDEDNESS: single
          (D) TOPOLOGY: linear (ii) MOLECULE TYPE: DNA (genomic)

(ix) FEATURE:
          (A) NAME/KEY: CDS
          (B) LOCATION: 1..294

(xi) SEQUENCE DESCRIPTION: SEQ ID NO:3:
```

```
ATG AAA GTT TCT GCA GTG CTT CTG TGC CTG CTG CTC ATG ACA GCA GCT    48
Met Lys Val Ser Ala Val Leu Leu Cys Leu Leu Leu Met Thr Ala Ala
 1               5                  10                  15

TTC AAC CCC CAG GGA CTT GCT CAG CCA GAT GCA CTC AAC GTC CCA TCT    96
Phe Asn Pro Gln Gly Leu Ala Gln Pro Asp Ala Leu Asn Val Pro Ser
                20                  25                  30

ACT TGC TGC TTC ACA TTT AGC AGT AAG AAG ATC TCC TTG CAG AGG CTG   144
Thr Cys Cys Phe Thr Phe Ser Ser Lys Lys Ile Ser Leu Gln Arg Leu
            35                  40                  45

AAG AGC TAT GTG ATC ACC ACC AGC AGG TGT CCC CAG AAG GCT GTC ATC   192
Lys Ser Tyr Val Ile Thr Thr Ser Arg Cys Pro Gln Lys Ala Val Ile
        50                  55                  60

TTC AGA ACC AAA CTG GGC AAG GAG ATC TGT GCT GAC CCA AAG GAG AAG   240
Phe Arg Thr Lys Leu Gly Lys Glu Ile Cys Ala Asp Pro Lys Glu Lys
65                  70                  75                  80

TGG GTC CAG AAT TAT ATG AAA CAC CTG GGC CGG AAA GCT CAC ACC CTG   288
Trp Val Gln Asn Tyr Met Lys His Leu Gly Arg Lys Ala His Thr Leu
                85                  90                  95

AAG ACT TGA                                                       297
Lys Thr (2) INFORMATION FOR SEQ ID NO:4:

(i) SEQUENCE CHARACTERISTICS:
         (A) LENGTH: 98 amino acids
         (B) TYPE: amino acid
         (D) TOPOLOGY: linear (ii) MOLECULE TYPE: protein (xi) SEQUENCE DESCRIPTION: SEQ ID NO:4:

Met Lys Val Ser Ala Val Leu Leu Cys Leu Leu Leu Met Thr Ala Ala
 1               5                  10                  15

Phe Asn Pro Gln Gly Leu Ala Gln Pro Asp Ala Leu Asn Val Pro Ser
                20                  25                  30

Thr Cys Cys Phe Thr Phe Ser Ser Lys Lys Ile Ser Leu Gln Arg Leu
            35                  40                  45

Lys Ser Tyr Val Ile Thr Thr Ser Arg Cys Pro Gln Lys Ala Val Ile
        50                  55                  60

Phe Arg Thr Lys Leu Gly Lys Glu Ile Cys Ala Asp Pro Lys Glu Lys
65                  70                  75                  80

Trp Val Gln Asn Tyr Met Lys His Leu Gly Arg Lys Ala His Thr Leu
                85                  90                  95

Lys Thr (2) INFORMATION FOR SEQ ID NO:5:

(i) SEQUENCE CHARACTERISTICS:
         (A) LENGTH: 26 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:5:

CCCGCATGCA AGCAGCAAGC AACTTT                                       26

(2) INFORMATION FOR SEQ ID NO:6:

(i) SEQUENCE CHARACTERISTICS:
         (A) LENGTH: 30 base pairs
```

(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:6:

AAAGGATCCC ATGTTCTTGA CTTTTTTACT                               30

(2) INFORMATION FOR SEQ ID NO:7:

(i) SEQUENCE CHARACTERISTICS:
    (A) LENGTH: 27 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:7:

CCCGCATGCA GCCAGATGCA CTCAACG                                  27

(2) INFORMATION FOR SEQ ID NO:8:

(i) SEQUENCE CHARACTERISTICS:
    (A) LENGTH: 28 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:8:

AAAGGATCCA GTCTTCAGGG TGTGAGCT                                 28

(2) INFORMATION FOR SEQ ID NO:9:

(i) SEQUENCE CHARACTERISTICS:
    (A) LENGTH: 29 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:9:

GGAAAGCTTA TGTGCTGTAC CAAGAGTTT                                29

(2) INFORMATION FOR SEQ ID NO:10:

(i) SEQUENCE CHARACTERISTICS:
    (A) LENGTH: 59 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:10:

CGCTCTAGAT TAAGCGTAGT CTGGGACGTC GTATGGGTAA CATGGTTCCT TGACTTTTT    59

(2) INFORMATION FOR SEQ ID NO:11:

(i) SEQUENCE CHARACTERISTICS:
    (A) LENGTH: 28 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:11:

GGAAAGCTTA TGAAAGTTTC TGCAGTGC                                              28

(2) INFORMATION FOR SEQ ID NO:12:

(i) SEQUENCE CHARACTERISTICS:
        (A) LENGTH: 58 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

CGCTCTAGAT CAAGCGTAGT CTGGGACGTC GTATGGGTAA GTCTTCAGGG TGTGAGCT            58

(2) INFORMATION FOR SEQ ID NO:13:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

CGCGGGATCC TTAACCTTCA ACATGAAA                                              28

(2) INFORMATION FOR SEQ ID NO:14:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

CGCGGGTACC TTAACACATA GTACATTTT                                             29

(2) INFORMATION FOR SEQ ID NO:15:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:15:

GCGGGATCCT TAACCTTCAA CATGAAA                                               27

(2) INFORMATION FOR SEQ ID NO:16:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:16:

```
CGCGGGTACC TTAACACATA GTACATTTT                                              29
```

(2) INFORMATION FOR SEQ ID NO:17:

(i) SEQUENCE CHARACTERISTICS:
        (A) LENGTH: 70 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:17:

```
His Pro Gly Ile Pro Ser Ala Cys Cys Phe Arg Val Thr Asn Ile Cys
1               5                   10                  15

Lys Ile Ser Phe Gln Ala Leu Lys Ser Tyr Lys Ile Ile Thr Ser Ser
            20                  25                  30

Lys Cys Pro Gln Thr Ala Ile Val Phe Glu Ile Lys Pro Asp Lys Met
        35                  40                  45

Ile Cys Ala Asp Pro Arg Xaa Xaa Trp Val Gln Asp Ala Lys Lys Tyr
    50                  55                  60

Leu Asp Gln Ile Ser Gln
65                  70
```

(2) INFORMATION FOR SEQ ID NO:18:

(i) SEQUENCE CHARACTERISTICS:
        (A) LENGTH: 99 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:18:

```
Met Lys Ala Ser Ala Ala Leu Leu Cys Leu Leu Leu Thr Ala Ala Ala
1               5                   10                  15

Phe Ser Pro Gln Gly Leu Ala Gln Pro Val Gly Ile Asn Thr Ser Thr
            20                  25                  30

Thr Cys Cys Tyr Arg Phe Ile Asn Lys Lys Ile Pro Lys Gln Arg Leu
        35                  40                  45

Glu Ser Tyr Arg Arg Thr Thr Ser Ser His Cys Pro Arg Glu Ala Val
    50                  55                  60

Ile Phe Lys Thr Lys Leu Asp Lys Glu Ile Cys Ala Asp Pro Thr Gln
65                  70                  75                  80

Lys Trp Val Gln Asp Phe Met Lys His Leu Asp Lys Lys Thr Gln Thr
                85                  90                  95

Pro Lys Leu
```

(2) INFORMATION FOR SEQ ID NO:19:

(i) SEQUENCE CHARACTERISTICS:
        (A) LENGTH: 76 amino acids
        (B) TYPE: amino acid
        (C) STRANDEDNESS: single
        (D) TOPOLOGY: linear (ii) MOLECULE TYPE: DNA (genomic)

(xi) SEQUENCE DESCRIPTION: SEQ ID NO:19:

```
Gln Pro Val Gly Ile Asn Thr Ser Thr Thr Cys Cys Tyr Arg Phe Ile
1               5                   10                  15
```

```
Asn Lys Lys Ile Pro Lys Gln Arg Leu Glu Ser Tyr Arg Arg Thr Thr
            20                  25                  30

Ser Ser His Cys Pro Arg Glu Ala Val Ile Phe Lys Thr Lys Leu Asp
        35                  40                  45

Lys Glu Ile Cys Ala Asp Pro Thr Gln Lys Trp Val Gln Asp Phe Met
    50                  55                  60

Lys His Leu Asp Lys Lys Thr Gln Thr Pro Lys Leu
65                  70                  75

(2) INFORMATION FOR SEQ ID NO:20:

(i) SEQUENCE CHARACTERISTICS:
        (A) LENGTH: 74 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:20:

Gly Pro Ala Ser Val Pro Thr Thr Cys Cys Phe Asn Leu Ala Asn Arg
1               5                   10                  15

Lys Ile Pro Leu Gln Arg Leu Glu Ser Tyr Arg Arg Ile Thr Ser Gly
            20                  25                  30

Lys Cys Pro Gln Lys Ala Val Ile Phe Lys Thr Lys Leu Ala Lys Asp
        35                  40                  45

Ile Cys Ala Asp Pro Lys Lys Lys Trp Val Gln Asp Ser Met Lys Tyr
    50                  55                  60

Leu Asp Gln Lys Ser Pro Thr Pro Lys Pro
65                  70
```